(12) United States Patent
Tal et al.

(10) Patent No.: US 12,133,958 B2
(45) Date of Patent: *Nov. 5, 2024

(54) DEPLOYING SPLIT-TIP HEMODIALYSIS CATHETER IN A RIGHT ATRIUM

(71) Applicant: Pristine Access Technologies LTD, Tel-Aviv (IL)

(72) Inventors: Michael Gabriel Tal, Tel Aviv (IL); Ron Livne, Tel-Aviv (IL); Rotem Neeman, Nirit (IL)

(73) Assignee: Pristine Access Technologies LTD., Franklin Lakes, NJ (US)

( * ) Notice: Subject to any disclaimer, the term of this patent is extended or adjusted under 35 U.S.C. 154(b) by 1031 days.

This patent is subject to a terminal disclaimer.

(21) Appl. No.: 17/005,586

(22) Filed: Aug. 28, 2020

(65) Prior Publication Data

US 2020/0390960 A1 Dec. 17, 2020

Related U.S. Application Data

(60) Division of application No. 15/598,009, filed on May 17, 2017, now Pat. No. 10,758,663, which is a
(Continued)

(51) Int. Cl.
*A61M 25/00* (2006.01)
*A61M 1/28* (2006.01)
(Continued)

(52) U.S. Cl.
CPC .......... *A61M 25/003* (2013.01); *A61M 1/285* (2013.01); *A61M 1/3661* (2014.02);
(Continued)

(58) Field of Classification Search
CPC ............ A61M 1/3661; A61M 25/0071; A61M 2025/0031; A61M 2205/0216; A61M 25/007

See application file for complete search history.

(56) References Cited

U.S. PATENT DOCUMENTS 5,156,592 A 10/1992 Martin et al.
5,800,414 A 9/1998 Cazal
(Continued)

FOREIGN PATENT DOCUMENTS

CN 101918066 A 7/2013
EP 1610853 A1 1/2006
(Continued)

OTHER PUBLICATIONS

Dec. 17, 2014 International Search Report issued in International Patent Application No. PCT/US2014/040935.
(Continued)

*Primary Examiner* — Leslie R Deak
(74) *Attorney, Agent, or Firm* — Rutan & Tucker LLP

(57) ABSTRACT

A split-tip catheter and methods for deploying a split-tip catheter in a right atrium are provided. The catheter is configured with a distal portion including a first and a second distal end regions elastically divergable from alignment along a splitting plane to regain a relaxed configuration. The first distal end region terminates in a first tip having a first forward opening, and the second distal end region terminates in a second tip having a second forward opening. Catheter deployment may include directing the first forward opening generally towards an anterior right atrium wall portion and applying the first forward opening to withdraw blood from the right atrium.

13 Claims, 19 Drawing Sheets

Related U.S. Application Data continuation-in-part of application No. 14/895,975, filed as application No. PCT/US2014/040935 on Apr. 4, 2014, now Pat. No. 10,363,390.

(60) Provisional application No. 61/939,158, filed on Feb. 12, 2014, provisional application No. 61/831,024, filed on Jun. 4, 2013.

(51) Int. Cl.
| | | |
|---|---|---|
| *A61M 1/36* | (2006.01) | |
| *A61M 25/01* | (2006.01) | |
| *B29C 67/00* | (2017.01) | |
| *B29L 31/00* | (2006.01) | |

(52) U.S. Cl.
CPC ...... *A61M 25/001* (2013.01); *A61M 25/0029* (2013.01); *A61M 25/0194* (2013.01); A61M 2025/0031 (2013.01); A61M 2025/0034 (2013.01); A61M 25/0071 (2013.01); A61M 2025/0073 (2013.01); A61M 2205/0216 (2013.01); A61M 2210/125 (2013.01); *B29C 67/0022* (2013.01); *B29L 2031/7542* (2013.01)

(56) References Cited

U.S. PATENT DOCUMENTS

| | | | |
|---|---|---|---|
| 5,947,953 | A | 9/1999 | Ash et al. |
| 6,001,079 | A | 12/1999 | Pourchez |
| 6,482,169 | B1 | 11/2002 | Kuhle |
| 6,513,527 | B1 | 2/2003 | Abdel-Aziz |
| 7,108,674 | B2 | 9/2006 | Quinn |
| 7,182,746 | B2 | 2/2007 | Haarala et al. |
| 7,776,005 | B2 | 8/2010 | Haggstrom et al. |
| 8,066,660 | B2 | 11/2011 | Gregersen et al. |
| 8,092,415 | B2 | 1/2012 | Moehle et al. |
| 10,758,663 | B2 * | 9/2020 | Tal .................. A61M 1/3661 |
| 2002/0052641 | A1 | 5/2002 | Monroe et al. |
| 2002/0062129 | A1 | 5/2002 | Mikus et al. |
| 2003/0153898 | A1 | 8/2003 | Schon et al. |
| 2004/0092863 | A1 | 5/2004 | Raulerson et al. |
| 2004/0167463 | A1 | 8/2004 | Zawacki et al. |
| 2005/0054989 | A1 | 3/2005 | McGuckin et al. |
| 2005/0277862 | A1 | 12/2005 | Anand |
| 2006/0025781 | A1 | 2/2006 | Young et al. |
| 2006/0149350 | A1 | 7/2006 | Patel et al. |
| 2007/0208276 | A1 | 9/2007 | Volk et al. |
| 2007/0225661 | A1 | 9/2007 | Ash et al. |
| 2009/0137944 | A1 | 5/2009 | Haarala et al. |
| 2009/0204052 | A1 | 8/2009 | Nimkar et al. |
| 2009/0204079 | A1 | 8/2009 | Nimkar et al. |
| 2009/0209940 | A1 | 8/2009 | Nimkar et al. |
| 2011/0011525 | A1 | 1/2011 | Sanscoucy |
| 2012/0130392 | A1 | 5/2012 | Levy et al. |
| 2012/0143123 | A1 | 6/2012 | Agnew |
| 2012/0179102 | A1 | 7/2012 | Blanchard et al. |
| 2013/0324964 | A1 * | 12/2013 | Florescu .......... A61M 25/0032 604/523 |
| 2014/0261407 | A1 | 9/2014 | Roberts et al. |
| 2015/0080762 | A1 | 3/2015 | Kassab et al. |

FOREIGN PATENT DOCUMENTS

| | | |
|---|---|---|
| EP | 1792637 A3 | 3/2008 |
| EP | 2277579 A1 | 1/2011 |
| EP | 2446915 B1 | 1/2018 |
| WO | 9115255 A1 | 10/1991 |
| WO | 1997009086 A1 | 3/1997 |
| WO | 2003045464 A2 | 6/2003 |
| WO | 2014197614 A2 | 12/2014 |

OTHER PUBLICATIONS

ISR received for PCT Application No. PCT/IB2016/054317, mailed Nov. 15, 2016, 5 pages.

Thomas Vesely et al., "Optimizing Hemodialysis Catheter Use," Endovascular Today, Jun. 2012, pp. 1-12.

U.S. Appl. No. 16/228,318, filed Dec. 20, 2018 Notice of Allowance dated May 12, 2021.

* cited by examiner

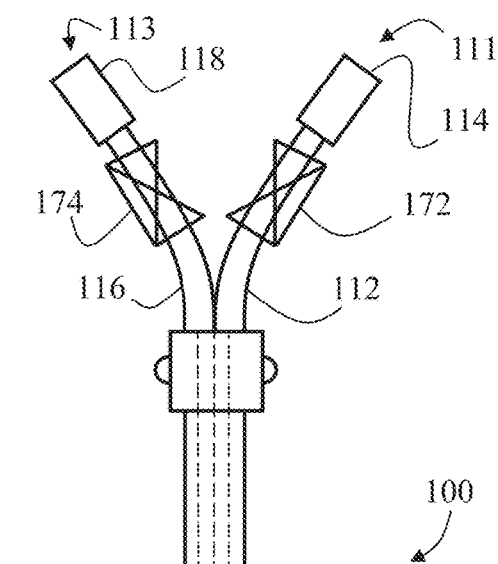
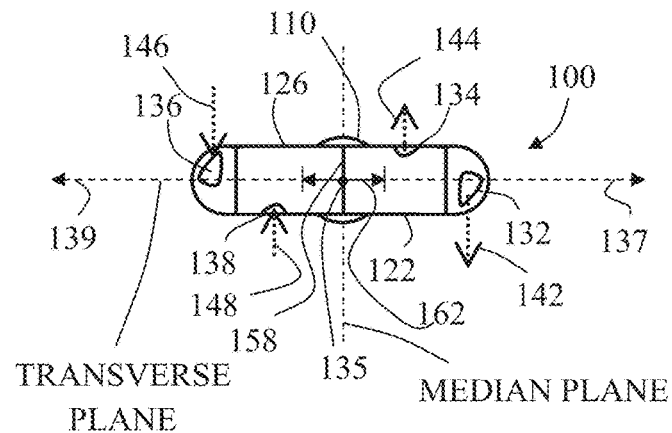
FIG. 1B
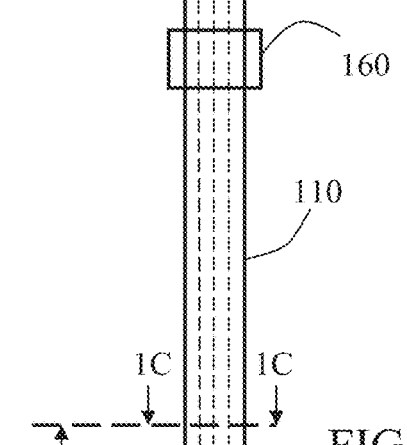
FIG. 1A
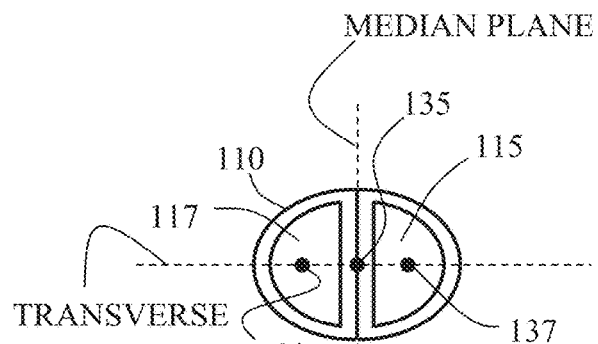
FIG. 1C
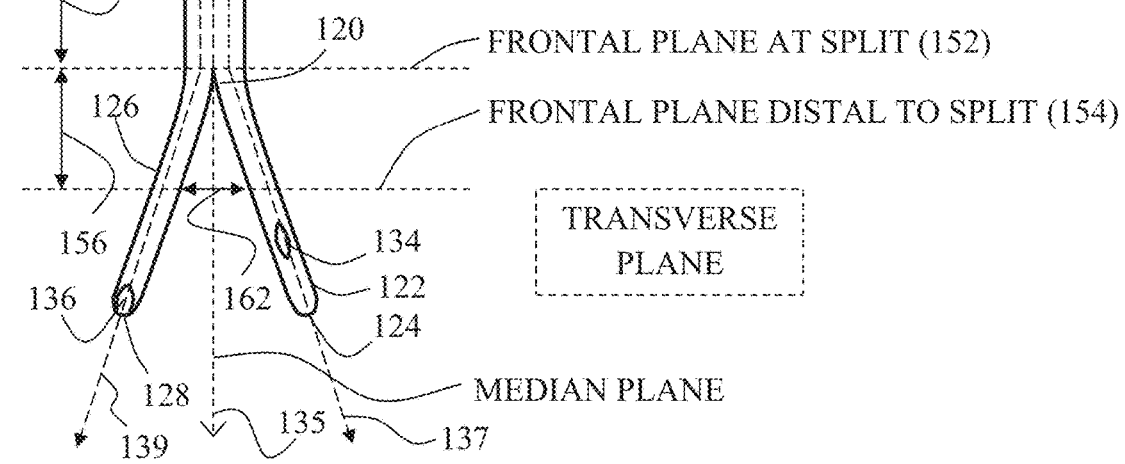

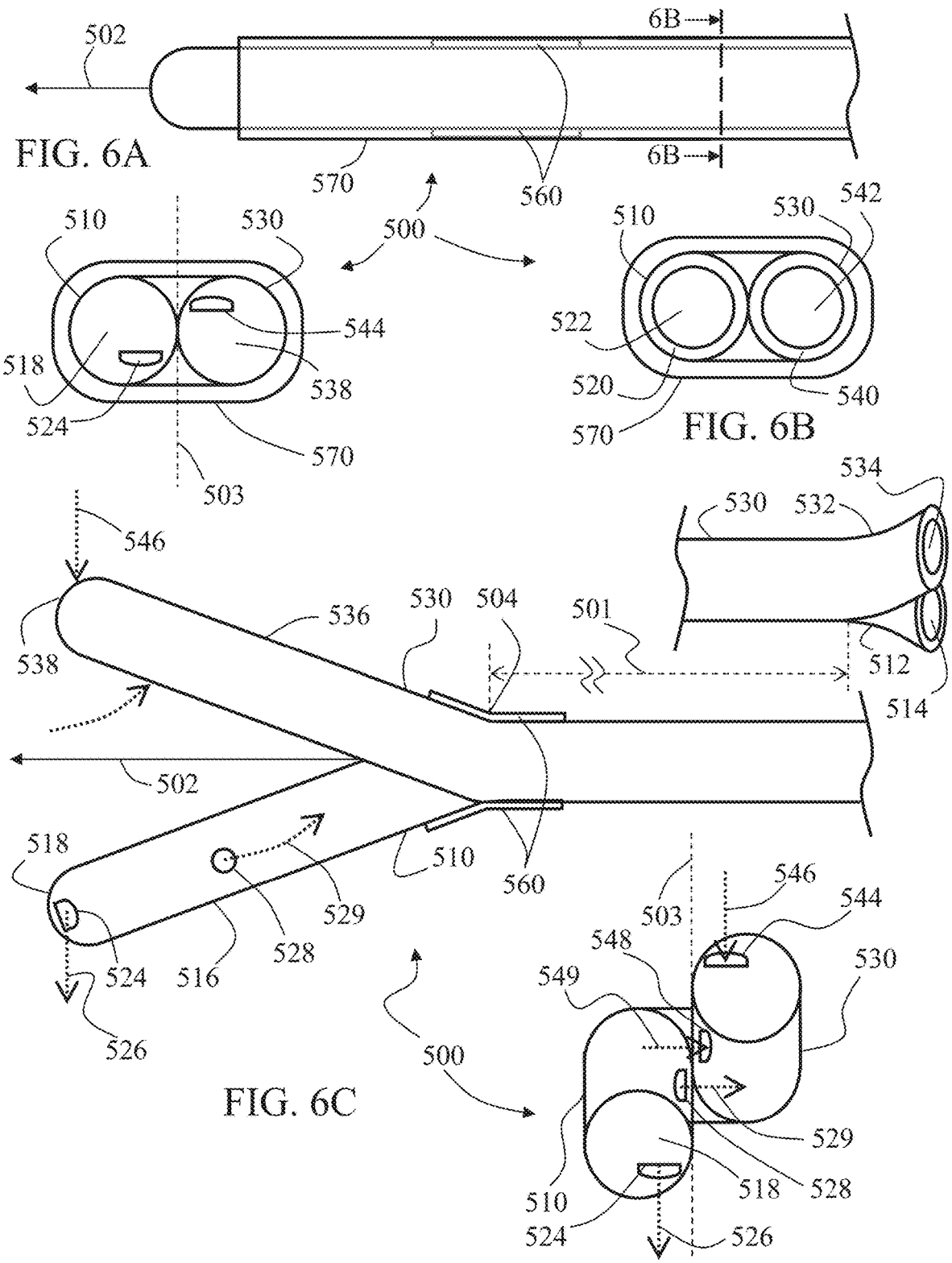

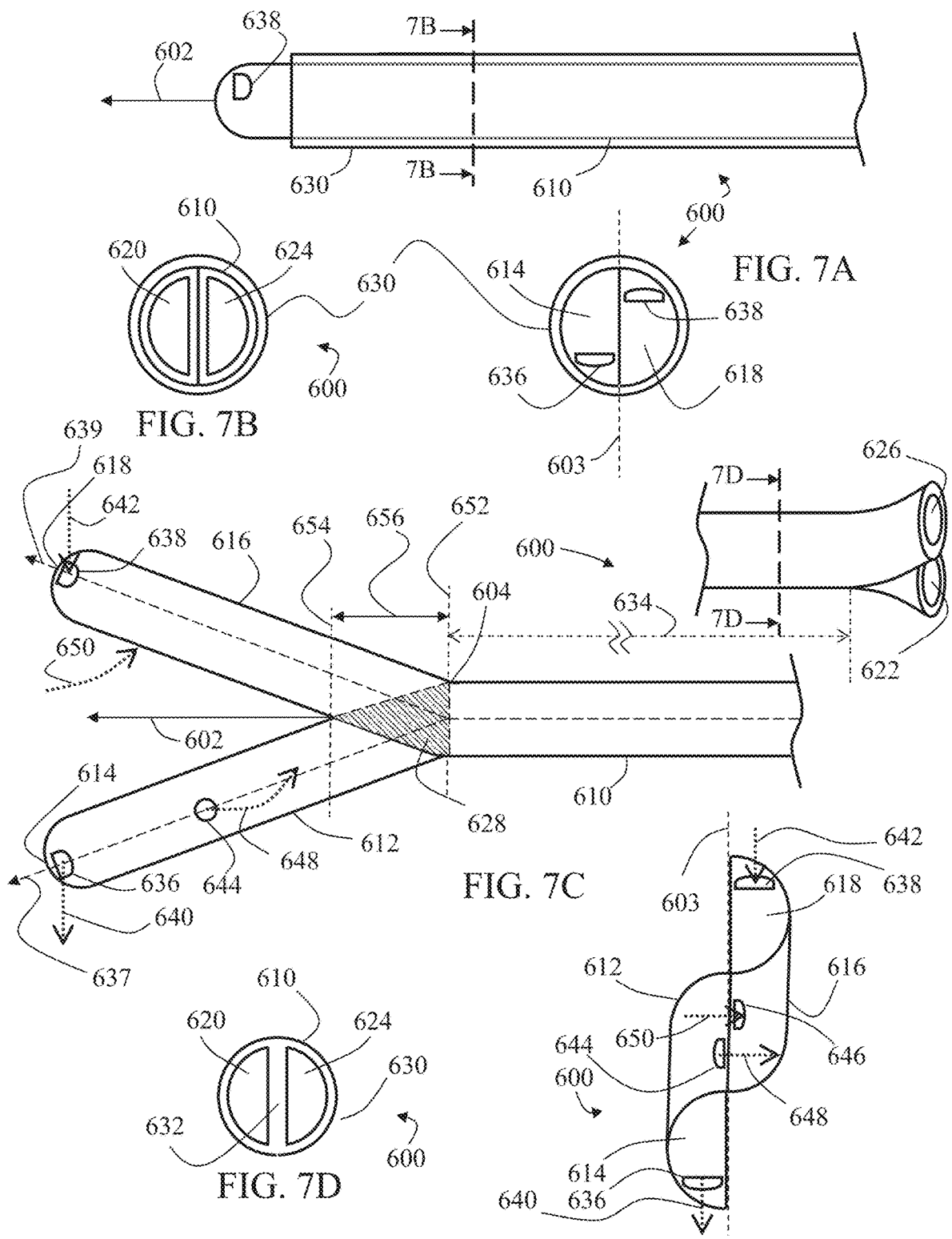

FIG. 9A
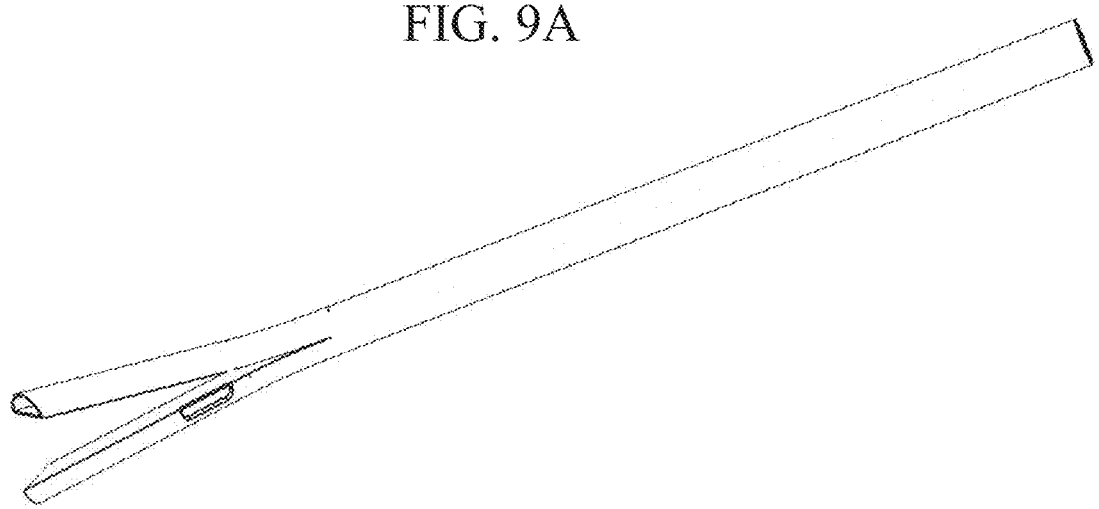
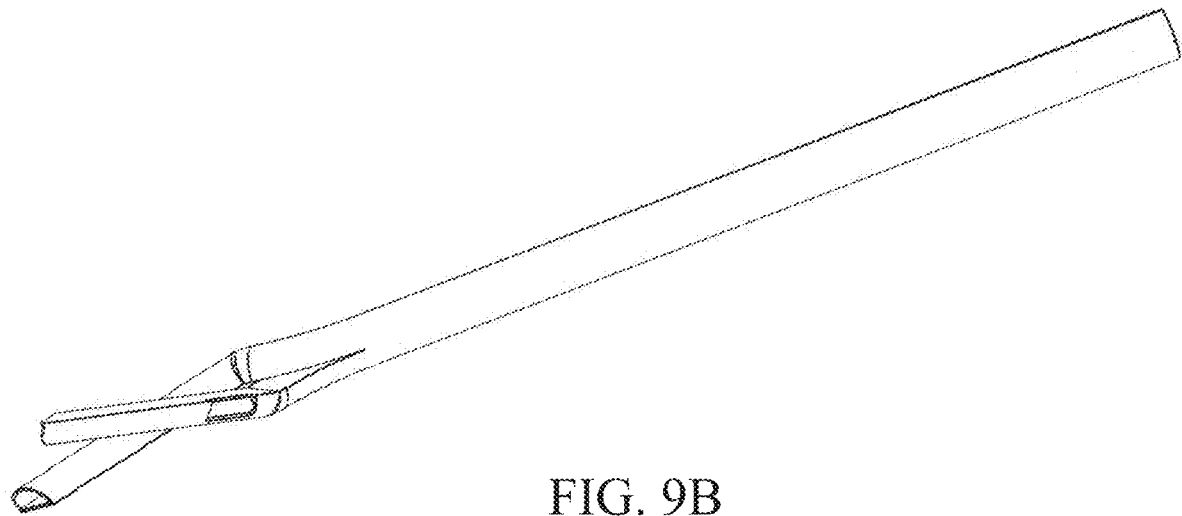
FIG. 9B

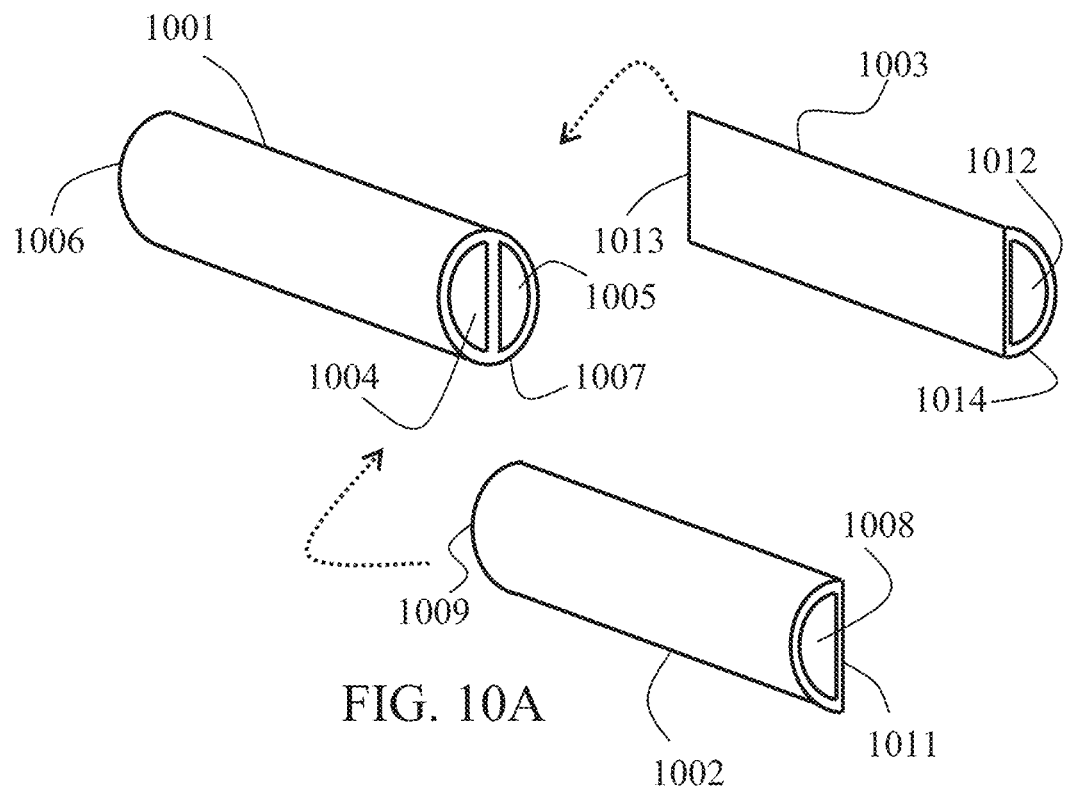
FIG. 10A
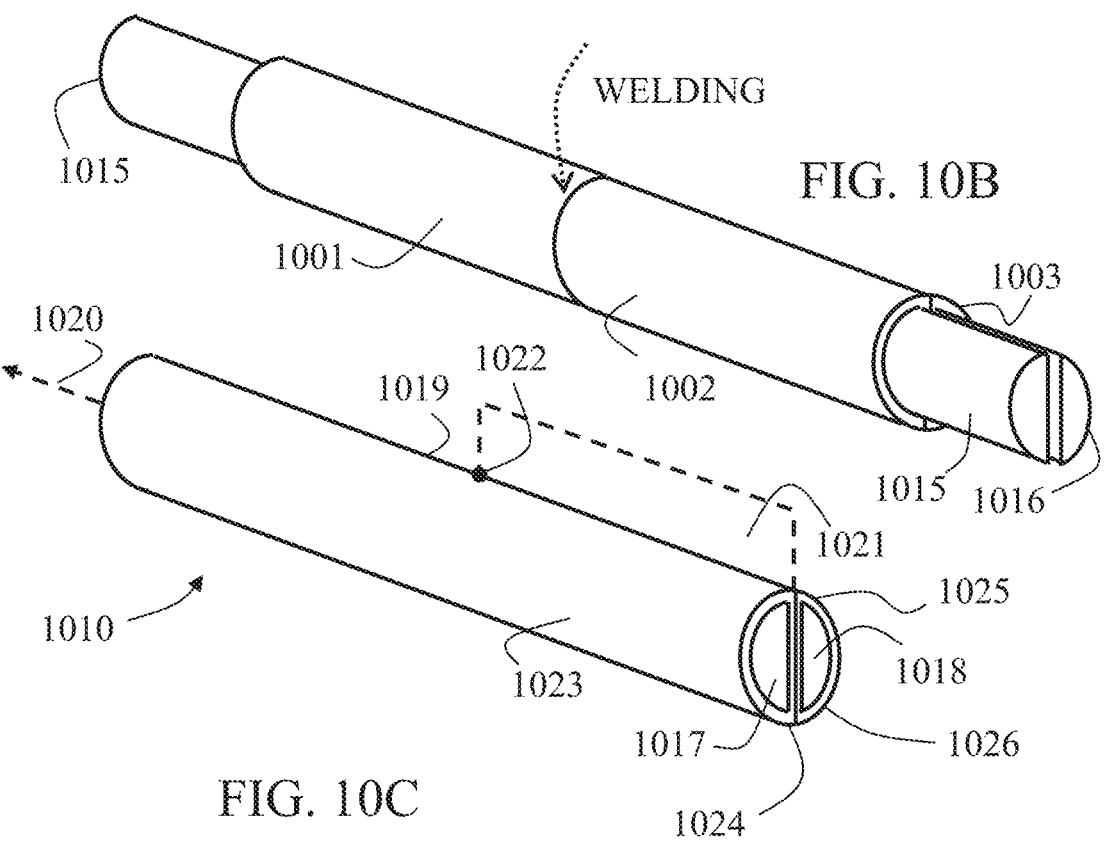
FIG. 10B
FIG. 10C

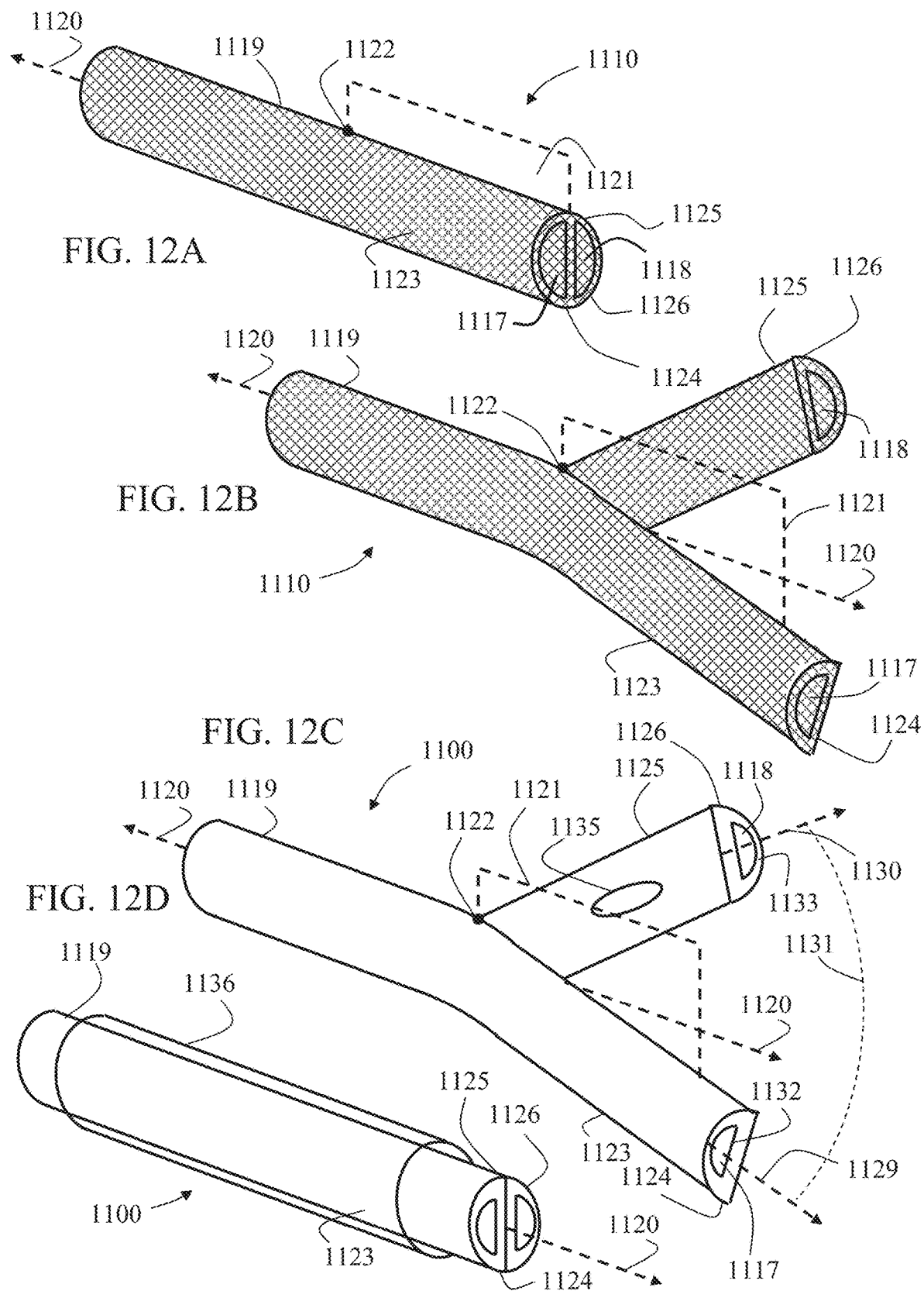

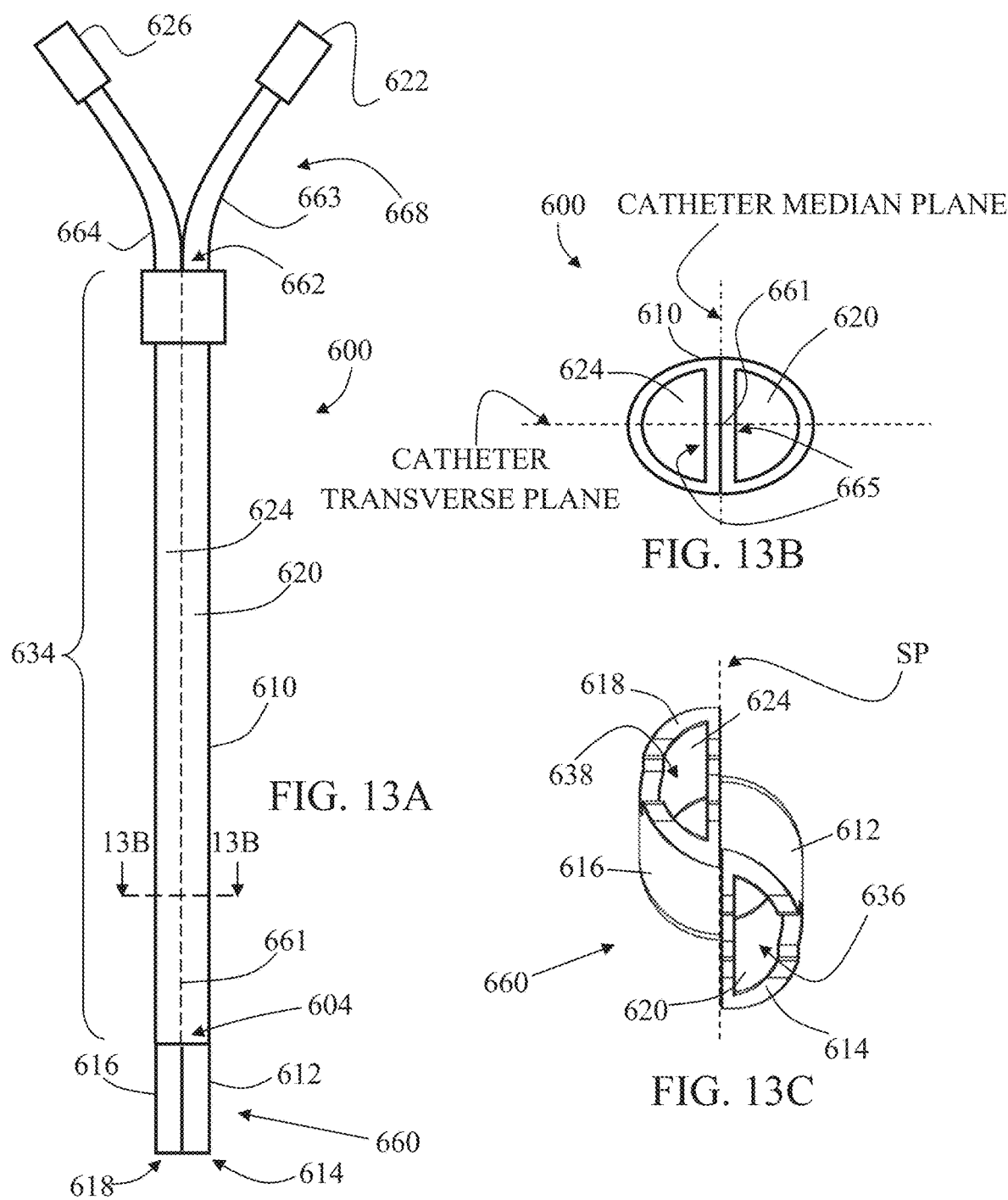

FRONTAL VIEW

RIGHT SIDE VIEW
SAGITTAL SECTION

SUPERIOR VIEW
TRANSVERSE SECTION

DEPLOYING SPLIT-TIP HEMODIALYSIS CATHETER IN A RIGHT ATRIUM

CROSS-REFERENCE TO RELATED APPLICATIONS

This application is a divisional of U.S. patent application Ser. No. 15/598,009, filed on May 17, 2017, now U.S. Pat. No. 10,758,663, which is a continuation-in-part (CIP) of U.S. patent application Ser. No. 14/895,975, filed Dec. 4, 2015, now U.S. Pat. No. 10,363,390, titled: "DUAL-TIP HEMODIALYSIS CATHETER", which is a National Phase of PCT Patent Application No. PCT/US2014/040935, filed Jun. 4, 2014, which claims the benefit of priority under 35 USC § 119(e) from U.S. Provisional Patent Application No. 61/831,024, filed Jun. 4, 2013, and from U.S. Provisional Patent Application No. 61/939,158, filed Feb. 12, 2014. The contents of all the above applications are fully incorporated herein by reference in their entireties, as if fully set forth herein.

FIELD AND BACKGROUND OF THE INVENTION

The present invention, in some embodiments thereof, relates to medical catheter apparatus and in particular to dialysis catheters having dual or split tip.

Split-tip dialysis catheters are mostly used in current days for chronic use of exchanging blood to and from the patient and the hemodialysis machine. During an exemplary hemodialysis procedure, a multiple lumen catheter is inserted into a body and blood is withdrawn through an arterial lumen of the catheter. This blood is supplied to a hemodialysis machine which dialyzes, or cleans, the blood to remove waste and excess water. The dialyzed blood is returned to the patient through a venous lumen of the catheter. Flow in the catheter may need to be reversed from time to time so that blood will flow in opposite direction in both arterial lumen and venous lumen to as mentioned above.

Some complications may occur in split tip catheters. At first, recirculation of blood flow is a known phenomenon in which the dialyzed blood exiting a catheter's lumen is directly returned to the other lumen without efficiently affecting surroundings. Another complication of hemodialysis catheters is flow occlusion. Flow occlusion is primarily caused by blockage of the arterial lumen. Common causes of occlusion are fibrin sheath formation, thrombus formation and positional occlusion. With positional occlusion of the catheter, there can be difficulty in removing blood from the patient. For example, a tip of the catheter has, to some extent, freedom of movement inside the patient, and this can cause occlusion, as a tip of the catheter or a side hole may be sucked against a blood vessel or heart wall.

In addition, split or dual tip dialysis catheters pose a unique feature in their current design, which makes them more prone to clotting complications. The area immediately below the separation zone of the two lumens (i.e., immediately distal to the junction) is a source of problem. With current known designs, in which the two lumens are separated directly away from each other, there is a dead space with slow and turbulent flow which makes this area very likely to form a clot. Those blood clots are a major complication of split tip dialysis catheters and are associated with increased morbidity.

The following patent documents are believed to represent the current state of the art: U.S. Pat. Nos. 5,800,414; 5,947,953; 7,108,674; 7,182,746; 7,776,005; 8,066,660; and 8,092,415.

SUMMARY OF THE INVENTION

According to an aspect of some embodiments of the present invention there is provided a method for deploying a split-tip catheter in a right atrium in a heart of a live subject, the method comprising:
  inserting a distal portion of the split-tip catheter into the right atrium via a superior vena cava, the distal portion includes a first distal end region terminating in a first tip having a first forward opening, and a second distal end region terminating in a second tip having a second forward opening; and
  fixating the split-tip catheter to the subject, wherein the first forward opening is directed generally towards an anterior right atrium wall portion.

In some embodiments, the method further comprising withdrawing blood from the right atrium through the first forward opening.

In some embodiments, the method further comprising delivering blood via the second forward opening into the right atrium.

In some embodiments, following the fixating, the second forward opening is directed generally away from the anterior right atrium wall portion.

In some embodiments, following the fixating, the second forward opening is directed generally towards a posterior right atrium wall portion.

In some embodiments, the first distal end region is directed from the superior vena cava generally towards the anterior right atrium wall portion.

In some embodiments, the second distal end region is directed from the superior vena cava generally towards the posterior right atrium wall portion.

In some embodiments, the split tip catheter includes a first lumen and a second lumen, the first lumen extends from a first proximal port to the first forward opening, and the second lumen extends from a second proximal port to the second forward opening, wherein the first lumen in the first distal end region and the second lumen in the second end region split from a shared boundary at a distal junction.

In some embodiments, the first lumen and the second lumen split from the shared boundary at a proximal junction into a proximal portion terminating in the first and second proximal ports.

In some embodiments, the method comprising:
  separating the first and second lumens to different directions, proximally to the proximal junction, along a first plane crossing through the shared boundary, and
  allowing split of the first and second lumens to different directions, distally to the distal junction, along a second plane crossing through the shared boundary and angled to the first plane.

In some embodiments, the allowing includes releasing the catheter distal portion.

In some embodiments, the separating includes releasing the catheter proximal portion.

In some embodiments, the second plane is perpendicular to the first plane.

In some embodiments, the fixating includes attaching the catheter proximal portion to outer surface of the live subject.

In some embodiments, the first and second proximal ports are lying side-by-side on outer skin surface of the live subject following the fixating.

In some embodiments, the fixating includes laying a mid-portion of the split-tip catheter along a subcutaneous path, the mid-portion extends between the proximal portion and the distal portion.

In some embodiments, following the fixating, the first and second lumens remain straight, untwisted or/and unturned with each other, throughout, and relative to, the shared boundary.

According to an aspect of some embodiments of the present invention there is provided a method comprising:

providing a split-tip catheter comprising a first lumen and a second lumen having a shared boundary from a proximal junction to a distal junction, the first and second lumens split at the distal junction into a first distal end region terminating in a first tip and a second distal end region terminating in a second tip, wherein the catheter is configured to have the first and second distal end regions elastically diverge from alignment along a splitting plane to regain a relaxed configuration;

delivering the first distal end region confined to alignment with the second distal end region in a superior vena cava opened to a right atrium of a subject; and releasing the first distal end region from alignment with the second distal end region, in the right atrium, by allowing the first distal end region to diverge along the splitting plane with the first tip shifting towards an anterior wall portion of the right atrium.

In some embodiments, the method further comprising withdrawing blood from the right atrium through a first forward opening provided at the first tip.

In some embodiments, the first distal end region is configured for withdrawing blood only from the first forward opening.

In some embodiments, the method further comprising orienting the splitting plane to parallel or to form an acute angle with a sagittal plane crossing the right atrium.

In some embodiments, the first and second lumens split at the proximal junction into a first proximal end region terminating in a first proximal port and a second proximal end region terminating in a second proximal port, wherein the method further comprising attaching a proximal portion of the catheter to outer surface of the subject with the first and second proximal end regions appositionally arranged on the subject outer surface.

In some embodiments, the orienting includes directing the split-tip catheter such that the splitting plane is perpendicular or oblique to the subject outer surface.

In some embodiments, following the attaching, the first proximal port points from the proximal junction towards a first direction, and, following the releasing, the first tip points from the distal junction towards a second direction, wherein the second direction is perpendicular to the first direction relative to a transverse plane crossing the right atrium.

In some embodiments, the catheter is configured to have the first and second distal end regions elastically diverge from alignment by applying a maximal lateral force sufficient to cut through or pull apart a naturally occurring fibrin sheath, wherein the delivering includes passing the split-tip catheter with the first and second distal end regions confined to alignment using removable aligning means through a tubular fibrin sheath structure, wherein the releasing includes removing the aligning means from the first and second distal end regions for allowing the first and second tips extending laterally.

In some embodiments, the delivering includes positioning an outer sheath in the tubular fibrin sheath structure and passing the split-tip catheter in the outer sheath whereby inner boundaries of the outer sheath impose the alignment of the first end region with the second distal end region; wherein the releasing includes pushing the first and second distal end regions to protrude out of the outer sheath to an extent sufficient to break portion of the fibrin structure. In some embodiments, the maximal lateral force is at least 50 gr.

According to an aspect of some embodiments of the present invention there is provided a split-tip catheter for hemodialysis comprising a first lumen and a second lumen having a shared boundary from a proximal junction to a distal junction, the first and second lumens split at the distal junction into a first distal end region terminating in a first tip and a second distal end region terminating in a second tip; wherein the catheter is configured to have the first and second distal end regions elastically diverge from alignment along a splitting plane to regain a relaxed configuration.

In some embodiments, the first distal end region is deliverable to a right atrium of a subject confined to alignment with the second distal end region using removable aligning means, and is configured for releasing from the aligning means in the right atrium, thereby diverging along the splitting plane with the first tip shifting towards an anterior wall portion of the right atrium.

In some embodiments, the split-tip catheter further comprising a first proximal port connectable to hemodialysis machine and having fluid communication with a first forward opening in the first tip, the split-tip catheter is configured such that, after deployment thereof into extending through a subcutaneous path and a superior vena cava, with the first and second distal end regions provided in the right atrium, the first proximal port points from the proximal junction towards a first direction, and the first tip points from the distal junction towards a second direction, wherein the second direction is perpendicular to the first direction relative to a transverse plane crossing the right atrium.

According to an aspect of some embodiments of the present invention there is provided a catheter assembly which comprises a first lumen having a first longitudinal axis extending along the center of the first lumen, and a second lumen having a second longitudinal axis extending along the center of the second lumen. In some embodiments, when the catheter is in a relaxed configuration the first and second longitudinal axes of the lumens are parallel over a proximal portion of the catheter and diverge over a distal portion of the catheter.

In some embodiments, the first and second longitudinal axes define a transverse plane that contains both the first and second longitudinal axes in the proximal portion of the catheter. Optionally, the first and second longitudinal axes further define a median plane parallel to and between the first and second longitudinal axes in the proximal portion of the catheter.

In some embodiments, over the distal portion of the catheter where the first and second longitudinal axes diverge, at least one of the first and second longitudinal axes diverges from the transverse plane when the catheter is in the relaxed configuration. Optionally, additionally or alternatively, over the distal portion of the catheter where the first and second longitudinal axes diverge from each other, the first longitudinal axis and the second longitudinal axis each remain approximately the same perpendicular distance from the median plane.

In some embodiments, in the relaxed configuration, the longitudinal axis of at least one of the first and second lumens diverges at least one centimeter away from the transverse plane at the tip of the diverging lumen. Optionally, in the relaxed configuration, the longitudinal axes of both of the first and second lumens diverge less than five millimeters farther away from the median plane at the tip of the diverging lumens.

In an aspect of some embodiments in accordance with the present disclosure, there is provided a catheter comprising a first lumen defined by a first lumen wall and a second lumen defined by a second lumen wall. In some embodiments, the catheter comprises a proximal portion where the first lumen wall and the second lumen wall are connected with each other to extend in parallel with each other, a distal portion where the first lumen wall and the second lumen wall are not parallel with each other when the catheter is in a relaxed configuration, and a junction portion where the first lumen wall and the second lumen wall contact each other, but the first lumen wall and the second lumen wall do not extend parallel to each other.

In an aspect of some embodiments in accordance with the present disclosure, there is provided a split tip dialysis catheter comprising an unsplit proximal portion, a split distal portion and a junction where the unsplit proximal portion splits to form the split distal portion. The catheter also includes a junction portion in the split distal portion and distal to the junction comprising a portion of the dialysis catheter having facing planar lumen walls. In some embodiments, the dihedral angle formed by the intersection of the planes defined by the facing planar lumen walls is less than 10 degrees when the catheter is in a relaxed configuration. In some embodiments, the dihedral angle is less than 5 degrees, optionally less than 1 degree. Optionally, no gap or crack greater than 0.5 mm is present in the junction portion. Optionally, the junction portion is the portion of the catheter extending 5 mm distal to the split, optionally 10 mm distal to the split, or optionally 20 mm distal to the split.

In an aspect of some embodiments in accordance with the present disclosure, there is provided a hemodialysis catheter, comprising an elongated body extendable along a longitudinal axis longitudinally split relative to a splitting plane at a junction into a first distal end region terminating in a first tip and a second distal end region terminating in a second tip. In some embodiments, the elongated body encloses a first lumen extending between a first proximal port and the first tip, and a second lumen extending between a second proximal port and the second tip. In some embodiments, the elongated body comprises an elastic portion or elastic member, about the junction, having a non-stressed form at the first end region and the second end region being separated with each other along the splitting plane with no gap therebetween adjacent the junction. In some embodiments, the first lumen and the second lumen are independent one to the other for facilitating simultaneous flow in opposite directions.

In some embodiments, the catheter includes removable aligning means aligning the first distal end region together with the second distal end region to the longitudinal axis, wherein upon removal thereof, the first distal end region and the second distal end region can voluntarily slide against each other, such as in a scissor-like movement, along the splitting plane, up to the non-stressed form of said elastic portion or elastic member. Optionally, the removable aligning means includes a removable cover such as a peel away sheath. Optionally, a septum divides the first lumen and the second lumen along a non-splitting length of the elongated body.

In some embodiments, the second tip is in apposition to the first tip when the first distal end region and the second distal end region are aligned. Optionally, the first distal end region and the second end region are formed in rotational symmetry one with the other relative to the longitudinal axis and comprising a plurality of openings distributed and shaped in accordance with the rotational symmetry. Optionally, each of the first distal end region and the second distal end region comprises at least two openings shaped to direct flow passing therethrough in different directions.

In some embodiments, the first distal end region comprises a first forward opening located adjacent to the first tip and the second distal end region comprises a second forward opening located adjacent to the second tip. Optionally, the first forward opening is shaped such to direct flow passing therethrough in a first course having a first direction and wherein the second forward opening is shaped such to direct flow passing therethrough in a second course nonintersecting with the first course. Optionally, the first distal end region comprises a first lateral opening located proximally to the first forward opening, and the second distal end region comprises a second lateral opening located proximally to the second forward opening. Optionally, the first lateral opening is shaped such to direct flow passing therethrough away from the first direction. Optionally, the second lateral opening is shaped such to direct flow passing therethrough in or towards the first direction. Optionally, the first lateral opening is shaped such to direct flow passing therethrough vertically to the first direction.

In some embodiments, the first course having an orthogonal projection parallel to the splitting plane. Optionally, the splitting plane is a median plane of the hemodialysis catheter. Optionally, the first course having an orthogonal projection parallel to a transverse plane orthogonal to the splitting plane in same Cartesian coordinate system. Optionally, the first course having an orthogonal projection parallel to a frontal plane orthogonal to the splitting plane in same Cartesian coordinate system.

According to an aspect of some embodiments of the present invention there is provided a catheter assembly, which includes a first catheter and a second catheter merged along a length includes a longitudinal assembly axis. In some embodiments, the first catheter has a first proximal end region includes a first port, a first distal end region terminating in a first tip, and a first wall defining a first lumen extending longitudinally therethrough between the first port and the first tip. Optionally and additionally, the second catheter has a second proximal end region includes a second port, a second distal end region terminating in a second tip in apposition to the first tip, and a second wall defining a second lumen extending longitudinally therethrough between the second port and the second tip. In some embodiments, the first wall and the second wall are longitudinally split from each other at a junction positioned at or proximally to the first and second distal end regions. Optionally, the first distal end region and the second end region are formed rotationally symmetric one with the other relative to the longitudinal assembly axis.

In some embodiments, the first catheter includes a first forward opening located at the first tip and the second catheter includes a second forward opening located at the second tip, wherein the first forward opening is shaped such to direct flow passing therethrough in a first direction and wherein the second forward opening is shaped such to direct flow passing therethrough in a second direction opposite to the first direction. In some embodiments, the first catheter includes a first lateral opening located at the first distal end region proximal to the first forward opening, and the second catheter includes a second lateral opening located at the second distal end region proximal to the second forward opening.

In some embodiments, the first catheter and/or the second catheter comprises an elastic portion or elastic member, about the junction, having a non-stressed form at the first end region and the second end region being separated with each other along the splitting plane with no gap therebetween adjacent the junction.

In some embodiments, the catheter assembly comprises removable aligning means aligning the first distal end region together with the second distal end region to the longitudinal assembly axis, wherein upon removal thereof, the first distal end region and the second distal end region can voluntarily slide against each other, such as in a scissor-like movement, along the splitting plane, up to the non-stressed form of the elastic portion or elastic member.

According to an aspect of some embodiments of the present invention there is provided a hemodialysis catheter, which comprises an elongated body extendable along a longitudinal assembly axis and splitting at a junction into a first distal end region terminating in a first tip and a second distal end region terminating in a second tip.

In some embodiments, the elongated body encloses a first lumen extending between a first proximal port and the first tip, and a second lumen extending between a second proximal port and the second tip.

In some embodiments, the first distal end region and the second end region are formed in rotational symmetry one with the other relative to the longitudinal assembly axis, and comprises a plurality of openings distributed and shaped in accordance with the rotational symmetry.

In some embodiments, the elongated body comprises an elastic portion or elastic member, about the junction, having a non-stressed form at the first end region and the second end region being separated with each other along the splitting plane with no gap therebetween adjacent the junction.

In some embodiments, the hemodialysis catheter comprises removable aligning means aligning the first distal end region together with the second distal end region to the longitudinal assembly axis, wherein upon removal thereof, the first distal end region and the second distal end region can voluntarily slide against each other, such as in a scissor-like movement, along the splitting plane, up to the non-stressed form of the elastic portion or elastic member.

In an aspect of some embodiments in accordance with the present disclosure there is provided a method for forming a dual-tip catheter, which comprises at least one of the following steps (not necessarily in same order):

a. providing a preformed part of the catheter comprising an elongated body, extendable along a longitudinal axis, longitudinally split relative to a splitting plane at a junction into a first distal end region terminating in a first tip and a second distal end region terminating in a second tip, wherein the elongated body encloses a first passage extending along the longitudinal axis and opened at the first tip, and a second passage extending along the longitudinal axis and opened at the second tip;

b. inserting a first contoured mandrel in the first passage and a second contoured mandrel in the second passage, such that the first end region is held in a first contour imposed by the first contoured mandrel and the second end region is held in a second contour imposed by the second contoured mandrel;

c. treating the elongated body thereby relieving internal stresses thereof; and d. removing the first contoured mandrel from the first passage and the second contoured mandrel from the second passage, wherein the elongated body in a non-stressed form thereof has the first end region and the second end region separated with each other along the splitting plane with no gap therebetween adjacent the junction.

In some embodiments, each of the first contoured mandrel and the second contoured mandrel is fixedly angled or curved along length thereof. Optionally, the first contoured mandrel is congruent, or geometrically similar about corresponding angles or curvatures thereof, to the second contoured mandrel.

In some embodiments, the elongated body in a non-stressed form thereof has the first tip pointed towards a first direction and the second tip pointed towards a second direction angled to the first direction relative to the splitting plane. Optionally, both the first direction and the second form straight lines with the junction forming a plane angle therebetween in the splitting plane.

In some embodiments, the first end region held in the first contour and the second end region held in the second contour form rotational symmetry one with the other relative to the longitudinal axis. Optionally, each of the first distal end region and the second distal end region comprises at least one opening distributed and shaped in accordance with the rotational symmetry. Optionally, each of the first distal end region and the second distal end region comprises at least two openings shaped to direct flow passing therethrough in different directions. Optionally, the first distal end region comprises a first forward opening located adjacent to the first tip and the second distal end region comprises a second forward opening located adjacent to the second tip, wherein the first forward opening is shaped such to direct flow passing therethrough in a first course nonintersecting with a flow in a second course directed by the second forward opening. Optionally, the first distal end region comprises a first lateral opening located proximally to the first forward opening, and the second distal end region comprises a second lateral opening located proximally to the second forward opening.

In some embodiments, the method of forming the catheter further includes a step of heating the elongated body, such that the first passage is shaped in accordance with outer boundaries of the first contoured mandrel and the second passage is shaped in accordance with outer boundaries of the second contoured mandrel.

In some embodiments, the elongated body comprises an elastic portion or elastic member, across the junction. Optionally, the method of forming the catheter also includes a step of coupling removable aligning means for aligning the first distal end region together with the second distal end region to the longitudinal axis. In some embodiments. upon removal of the aligning means, the first distal end region and the second distal end region can voluntarily slide against each other, such as in a scissor-like movement, along the splitting plane, up to the non-stressed form. Optionally, the removable aligning means includes a removable cover such as a peel away sheath.

In some embodiments, the second tip is in apposition to the first tip when the first distal end region and the second distal end region are aligned.

In some embodiments, the elongated body is formed of a fluid sealed material whereby the first passage forms a first lumen and the second passage forms a second lumen sealed to the first lumen. Optionally, a septum divides the first lumen and the second lumen along a non-splitting length of the elongated body. Optionally, the fluid sealed material includes at least one of silicone rubber, polyurethane, polycarbonate-based thermoplastic polyurethanes and Carbothane.

In some embodiments, the preformed part is formed by at least one of the following steps (not necessarily in same order):

I. collecting a first preformed member, a second preformed member and a third preformed member, wherein the first preformed member encloses a plurality of lumens extending therealong and opened at both ends thereof, the second preformed member encloses one lumen extending therealong and opened at both ends thereof, and the third preformed member encloses one lumen extending therealong and opened at both ends thereof;

II. welding the second preformed member and the third preformed member to the first preformed member to form the elongated body, whereby one lumen of the first preformed member and the one lumen of the second preformed member forms the first passage, and other lumen of the first preformed member and the one lumen of the third preformed member forms the second passage;

III. inserting a first straight mandrel through the one lumen of the first preformed member and the one lumen of the second preformed member and a second straight mandrel through the other lumen of the first preformed member and the one lumen of the third preformed member; and IV. aligning and/or approximating the first, second and third preformed members over the first and second straight mandrels; and V. heating the first, second and/or third preformed members, or the welded elongated body, such that the first passage is shaped in accordance with outer boundaries of the first straight mandrel and the second passage is shaped in accordance with outer boundaries of the second straight mandrel.

In some embodiments, the preformed part is formed of a meshed structure. Optionally, the meshed structure comprises at least one helically wound filament. Optionally, the filament is made from metal, polymer, carbon and/or glass. In some embodiments, the method includes impregnating and/or coating the preformed part with a polymeric solution.

In some embodiments, treating the elongated body includes at least one of heat treatment, chemical treatment, hardening, and plastic deformation.

In some embodiments, treating the elongated body creates elastic resistivity to a deviation from the non-stressed form.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1C schematically illustrate an exemplary dual-tip hemodialysis catheter assembly, in accordance with embodiments of the present invention:

FIGS. 6A-6C schematically illustrate a catheter assembly, comprising a first catheter and a second catheter merged along a length comprising a longitudinal assembly axis, in accordance with embodiments of the present invention;

FIGS. 7A-7D schematically illustrate a hemodialysis catheter, comprising an elongated body extendable along a longitudinal assembly axis and longitudinally split from each other, in accordance with embodiments of the present invention:

FIGS. 9A-9B are perspective views of another embodiment of a hemodialysis catheter according to some embodiments.

FIGS. 10A-10G schematically illustrate different scenarios representing possible exemplary steps in a method for forming a dual-tip catheter, in accordance with embodiments of the present invention;

FIGS. 12A-12D schematically illustrate different scenarios representing possible exemplary steps in another method for forming a dual-tip catheter, in accordance with embodiments of the present invention:

FIGS. 13A-13C schematically illustrate a variation of the exemplary split-tip hemodialysis catheter of FIGS. 7A-D, in accordance with embodiments of the present invention;

DESCRIPTION OF EMBODIMENTS OF THE INVENTION

Figure 2:
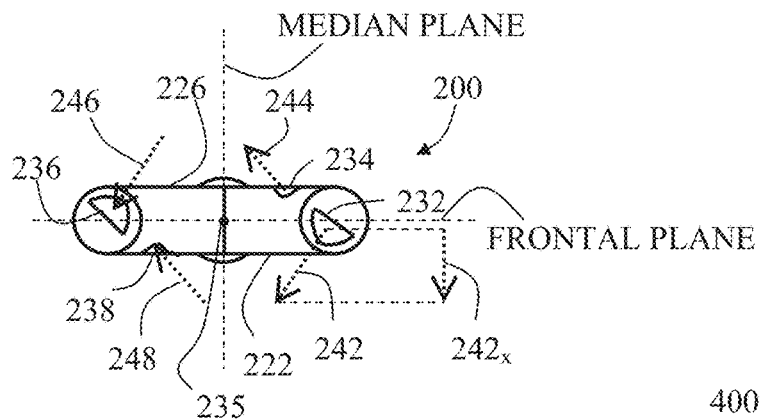
FIG. 2 schematically illustrates an exemplary dual-tip hemodialysis catheter assembly with partially facing distal openings, in accordance with embodiments of the present invention.

The following preferred embodiments may be described in the context of exemplary dialysis procedures for ease of description and understanding. However, the invention is not limited to the specifically described devices and methods, and may be adapted to various clinical applications without departing from the overall scope of the invention.

The present invention, in some embodiments thereof, relates to medical catheter apparatus and in particular to dialysis catheters having dual tip.

An aspect of some embodiments of the present invention relates to a catheter assembly, comprising a first catheter and a second catheter. In some embodiments, the catheter assembly is intended for hemodialysis process and is connectable to a hemodialysis machine wherein one catheter is set to deliver purified blood into the cardiovascular system and the other catheter is set to draw blood therefrom, and optionally occasionally reverse the blood circulation between these two catheters. In some embodiments, the first catheter and the second catheter are merged along a length comprising a longitudinal assembly axis, optionally until a distal splitting pointline and/or in-between a distal splitting point/line and a proximal splitting pointline.

In some embodiments, the first catheter has a first proximal end region including a first port, a first distal end region terminating in a first tip, and a first wall defining a first lumen extending longitudinally therethrough between the first port and the first tip. Optionally and additionally, the second catheter has a second proximal end region including a second port, a second distal end region terminating in a second tip, and a second wall defining a second lumen extending longitudinally therethrough between the second port and the second tip. In some embodiments, the first lumen and the second lumen are independent from each other for facilitating simultaneous flow in opposite directions. In some embodiments, the first wall and the second wall are longitudinally split from each other, optionally relative to a median plane at a splitting line or a junction positioned at or proximally to the first and second distal end regions. Optionally, the first distal end region of the first catheter and the second distal end region of the second catheter extend substantially the same from the splitting line or junction such that the second tip is in apposition to the first tip.

In some embodiments, a catheter assembly comprises a first lumen having a first longitudinal axis extending along the center of the first lumen and a second lumen having a second longitudinal axis extending along the center of the second lumen. When the catheter assembly is in a relaxed configuration the first and second longitudinal axes of the lumens are parallel over a proximal portion of the catheter and diverge over a distal portion of the catheter. The first and second longitudinal axes define a transverse plane that contains both the first and second longitudinal axes in the proximal portion of the catheter. The first and second longitudinal axes further define a median plane parallel to and between the first and second longitudinal axes in the intermediate portion of the catheter. Over the distal portion of the catheter where the first and second longitudinal axes diverge, at least one of the first and second longitudinal axes diverges from the transverse plane when the catheter is in the relaxed configuration.

In some embodiments, a catheter comprises a first lumen defined by a first lumen wall, a second lumen defined by a second lumen wall, a proximal portion where the first lumen wall and the second lumen wall are connected with each other to extend in parallel with each other, a distal portion where the first lumen wall and the second lumen wall are not in contact with each other such that when the catheter is in a relaxed configuration the first and second lumens diverge from each other, and an intermediate portion between the proximal portion and the distal portion where the first lumen wall and the second lumen wall contact each other, but the first lumen wall and the second lumen wall do not extend parallel to each other.

In some embodiments, a split tip dialysis catheter comprises a split distal portion, an unsplit proximal portion, and a crack-free junction between the split distal portion and the unsplit proximal portion when the catheter is in a relaxed configuration.

The first distal end region and the second end region may be substantially pliant to juxtaposingly conform to boundaries of a hosting vessel lumen. Optionally and alternatively, the first distal end region and the second end region are substantially elastic or rigid such that the first distal tip and the second distal tip are provided in a predetermined distance and/or relative positioning upon deployment. In some embodiments, the first distal end region and the second end region are rotationally symmetric one with the other relatively to the longitudinal assembly axis, optionally distanced similarly about a transverse plane (relatively to the median plane) and/or optionally distanced similarly about the median plane (relatively to the transverse plane). Rotational symmetry may include only the general shape and optionally contouring of the end regions or may also include openings number, size, shape and/or distribution between the end regions in rotational symmetry.

In some embodiments, the first catheter includes a first forward opening located at the first distal tip and the second catheter includes a second forward opening located at the second distal tip. Optionally, the first forward opening is shaped such to direct flow passing therethrough in a first direction having a Cartesian component parallel to the median plane and the second forward opening is shaped such to direct flow passing therethrough in a second direction opposite to the first direction.

In some embodiments, the first catheter includes a first lateral opening located at the first distal end region proximal to the first forward opening, and the second catheter includes a second lateral opening located at the second distal end region proximal to the second forward opening.

In some embodiments, the first lateral opening is shaped such to direct flow passing therethrough in opposite direction to the first direction and/or the second lateral opening is shaped such to direct flow passing therethrough in opposite direction to the second direction. Optionally and alternatively, the first lateral opening is shaped such to direct flow passing therethrough in same direction as the first direction and/or the second lateral opening is shaped such to direct flow passing therethrough in same direction as the second direction. Optionally and alternatively, the first lateral opening is shaped such to direct flow passing therethrough vertically to the first direction and/or the second lateral opening is shaped such to direct flow passing therethrough vertically to the second direction.

Referring now to the drawings, FIGS. 1A-1C schematically illustrate an exemplary dual-tip hemodialysis catheter assembly 100, in accordance with embodiments of the present invention. Set forth below are a variety of descriptions of the geometric configuration of the distal portions of catheters. As catheters are made of flexible material, they can of course be pushed, pulled, or stretched into a wide variety of configurations. Unless otherwise specified, such as describing a catheter in a sheath, the geometric configurations described herein are the configurations that the subject catheter naturally takes due to its inherent construction and material properties when the distal portion is in a "relaxed" or "non-stressed" state. FIGS. 1A and 1B illustrate the catheter in a "relaxed" or "non-stressed" configuration. The catheter is in a relaxed or non-stressed configuration when hanging freely downward as illustrated in FIG. 1A, being held or supported in the proximal region (such as region 159) with the distal portion that extends downward to the tips being free of external forces. As shown in FIG. 1, split or dual tip catheters typically have relaxed configurations where the walls forming individual lumens diverge from each other in the distal region of the catheter assembly.

Catheter assembly 100 includes an elongated body 110 merging a first catheter 111 forming walls enclosing a first lumen 115 and a second catheter 113 forming walls enclosing a second lumen 117 that is isolated from first lumen 115. Each lumen 115, 117 defines a longitudinal axis 137, 139 respectively, centrally located within and extending along the length of each lumen. The catheter assembly 100 further defines an assembly longitudinal axis 135 centrally located in the elongated body. Although the term "centrally located" should be clear to those in the art, for absence of doubt, for each lumen this means at the centroid of the cross sectional shape perpendicular to lumen extent (such as shown in FIG. 1C) as defined by the inner surface of the walls forming each lumen. For the catheter assembly as a whole this means at the centroid of the cross sectional shape perpendicular to lumen extent (such as shown in FIG. 1C) as defined by the outer surface of the elongated body 110. Optionally and as illustrated schematically, the catheters are merged along the longitudinal axis 135 up to a splitting point or line 120, also referred to herein as the junction. This point defines the location of a frontal plane 152 at the split or junction 120 that is perpendicular to the extent of the elongated body 110 at the point of the split 120. If the splitting line has a longitudinal extent, the position of the junction 120, and thus the frontal plane 152, is considered to be the proximal initiation point of the split.

The portion of the catheter assembly proximal to and within 2 cm of the frontal plane 152 is referred to as the connected or merged portion of the catheter assembly (designated 159 in FIG. 1A). In the connected or merged portion, the lumens extend parallel to each other. The portion of the catheter assembly distal to the frontal plane 152 to the most distal tip of the catheter assembly is referred to as the dual or split portion of the catheter assembly. In this split portion, the longitudinal axes of the lumens diverge from each other.

To facilitate explanation of the structure of some embodiments described herein, also defined in FIG. 1 is a frontal plane 154 distal to the split 120 that is parallel to the frontal plane 152 at the split 120. The portion of the catheter assembly 100 that is between the frontal plane 152 at the split 120 and the frontal plane 154 distal to the split 120 (designated 156 in FIG. 1A) is referred to herein as the "junction portion" of the catheter assembly and resides within the previously defined dual or split portion of the catheter assembly. The junction portion is considered to be the portion of the catheter assembly distal to but near the junction, and this can be defined as a variety of different distances. The junction portion 156 may be defined as the portion from the split to 5 mm distal of the split in some embodiments. The junction portion 156 may be defined as the portion from the split to 10 mm distal of the split in some embodiments. The junction portion 156 may be defined as the portion from the split to 20 mm distal of the split in some embodiments. As will be explained further below, in addition to being defined as a specific distance along the catheter distal from the split, the junction portion 156 may alternatively be defined functionally as a clot forming risk region distal to the split, or as another alternative structurally as an area of overlap or contact between the catheters distal to the split.

Also defined in FIG. 1 is a gap distance 162. This gap distance is defined as the perpendicular distance in the transverse plane between the inner surfaces of the split wall that face each other distal to the split 120 at the location of the frontal plane 154 that defines the distal extent of the junction portion 156. This gap distance will van with varying angles of separation of the two lumens distal to the split 120.

FIG. 1C schematically illustrates a cross section of the merged portion of catheter body 110 formed as a single double-lumen catheter portion in which lumens 115 and 117 are abutting and sharing a single separating wall; nevertheless this should be considered one of many alternative exemplary configurations; other possible configurations may include different multiple-lumen shapes or any connection or adjunction (e.g., by welding, gluing or otherwise) along a surface, a line and/or points of contact between first catheter 111 and second catheter 113. Optionally and alternatively, the two catheters are not merged and/or are detachably connectable along a length thereof. The embodiment of FIG. 1 as illustrated by FIG. 1C is known as a "double-D" type catheter assembly. Split or dual tip double-D type catheter assemblies are characterized by two approximately semi-circular lumens with adjacent flat sides defined by a centrally positioned substantially linear wall. The outer circumference of the catheter assembly in the merged portion is typically of approximately circular cross section. As shown in FIG. 1, when formed into a split or dual tip, the two lumens are separated by cutting through and along the shared centrally positioned substantially linear wall. The direction of the splitting line is therefore the same as the direction of the extent of the central wall in the junction portion of the catheter assembly. For double-D type catheters, the angle of separation of the two lumens may be a dihedral angle formed at the junction or splitting line 120 by the intersection of the planes defined by the inner planar surfaces of the two lumens in the junction portion 156. The double-D type split or dual tip catheter is an especially advantageous application of the embodiments described herein.

First catheter 111 has a first proximal end region 112 which includes a first proximal hub or port 114, and a first distal end region 122 terminating in a first tip 124 which includes a first forward opening 132, such that first lumen 115 extends between first port 114 and first forward opening 132. Likewise, second catheter 113 has a second proximal end region 116 which includes a second proximal hub or port 118, and a second distal end region 126 terminating in a second tip 128 which includes a second forward opening 136, such that second lumen 117 extends between second port 118 and second forward opening 136. Catheter assembly 100 may include connection tubing that has clamps on them (such as clamp 172 on first catheter 111 tubing and clamp 174 on second catheter 113 tubing), and it may have a cuff 160, optionally from Dacron or other materials, for in-growth purpose.

Catheter assembly 100 is configured to connect with a hemodialysis machine (connection can be facilitated via ports 114 and 118) such that one catheter can be set to deliver purified blood into the cardiovascular system and the other catheter can be set to draw blood therefrom, while occasionally the blood circulation may be reversed between these two catheters. First lumen 115 and second lumen 117 are independent from each other for facilitating simultaneous flow in opposite directions.

First catheter 111 and second catheter 113 split from a unitary form of body 110 at splitting line 120 such that their walls are longitudinally split from each other relatively to a median plane in a Cartesian coordinate system, which optionally includes and/or extends from longitudinal axis 135. Optionally and alternatively, both walls are split relatively to longitudinal axis 135 and not relatively to the median plane. Optionally, first distal end region 122 and second distal end region 126 extend substantially the same from the splitting line 120 such that second tip 128 is in apposition to first tip 124. Unlike nonsymmetrical split-tip dialysis catheters having distal end regions of different lengths, symmetrical hemodialysis catheter like catheter assembly 100 are believed to diminish the degree of unwanted dialyzed blood recirculation as may possibly occur between an upstream positioned lumen and a downstream positioned lumen.

First distal end region 122 and second distal end region 126 may be substantially pliant to conform (optionally, juxtaposingly) to boundaries of a hosting vessel lumen. Optionally and alternatively, first distal end region 122 and second distal end region 126 are substantially elastic or rigid such that first tip 124 and second tip 128 are provided in a predetermined distance and/or relative positioning upon deployment. In some embodiments, first distal end region 122 and second distal end region 126 are formed in a rotational symmetry by overall size and shape and/or openings size, shape and/or distribution, one with the other, relatively to longitudinal axis 135. Optionally and additionally, first distal end region 122 and second distal end region 126 are distanced similarly about a transverse plane (being orthogonal to the median plane in the same Cartesian coordinate system) and/or optionally distanced similarly about median plane 130.

Catheter assembly 100 includes distal openings for local blood dispersion and collection; all openings are shaped and distributed on distal end regions 122 and 126 while maintaining rotational symmetry around longitudinal axis 135. Preferably and as shown, first distal end region 122 and second distal end region 126 are rotationally symmetric yet asymmetric (i.e., are not mirrored), and, as in this example, optionally inverted, with respect to the median plane, in order to minimize potential unwanted recirculation of dialyzed blood between adjacent openings. First forward opening 132 is shaped such to direct flow passing therethrough in a first course with a first direction 142 (show-n in FIG. 1B as an outflow but can be reversed to inflow). Likewise, second forward opening 136 is shaped such to direct flow passing therethrough in a second course being nonintersecting with, and optionally parallel to, the first course yet have a second direction 146 which is opposite to first direction 142, meaning that a stream flowing out of first forward opening 132 in first direction 142 shall travel farthest away from second forward opening 136, and vice versa: a stream flowing out of second forward opening 136 opposite to second direction 146 shall travel farthest away from first forward opening 132. The two flow courses may projected in any orientation in space, as represented in a Cartesian coordinate system, including median, transverse and frontal planes, and may include orthogonal projections (i.e., being different than 0) in at least one of these planes. In some embodiments, both directions 142 and 146 are not directed laterally away from median plane 130 in order to avoid suction of adjacent vascular wall tissue.

Nevertheless, in order to avoid potential flow occlusion in case of choking of any of the forward openings, lateral openings are also provided, situated distally to the forward openings. Therefore, first catheter 111 includes a first lateral opening 134 located at first distal end region 122 proximal to first forward opening 132, and second catheter 113 includes a second lateral opening 138 located at second distal end region 126 proximal to second forward opening 128. First lateral opening 134 is shaped such to direct flow passing therethrough in a third direction 144 which is opposite to first direction 142. Likewise, second lateral opening 138 is shaped such to direct flow passing therethrough in a fourth direction 148 which is opposite to second direction 146.

FIG. 2 schematically illustrates an exemplary dual-tip hemodialysis catheter assembly 200 with partially facing distal openings, in accordance with embodiments of the present invention. Catheter assembly 200 resembles catheter assembly 100 except that openings are shape and oriented such that flow is directing to or from a catheter median plane, at least in part. Catheter assembly 200 includes two partially merged catheters. The first catheter has a first distal end region 222 terminating in a first tip which includes a first forward opening 232 and the second catheter has a second distal end region 226 terminating in a second tip which includes a second forward opening 236. First distal end region 222 and second distal end region 226 extend substantially the same from the splitting line such that second tip 228 is in apposition to first tip 224, and are formed rotationally symmetric by overall size and shape and/or openings size, shape and/or distribution, one with the other, relatively to longitudinal axis 235. Optionally and additionally, first distal end region 222 and second distal end region 226 are distanced similarly about a transverse plane (being orthogonal to the median plane in the same cartesian coordinate system) and/or optionally distanced similarly about the median plane.

Catheter assembly 200 includes distal openings for local blood dispersion and collection; all openings are shaped and distributed on distal end regions 222 and 226 while maintaining rotational symmetry around longitudinal axis 235. First forward opening 232 is shaped such to direct flow passing therethrough in a first direction 242 (shown in FIG. 2 as an outflow but can be reversed to inflow). As shown, first direction 242 is directed towards the median plane and away from the transverse plane, and comprising an orthogonal projection $242_x$ to median plane 230, which is orthogonal both to the transverse plane and the frontal plane in same Cartesian coordinate system. Likewise, second forward opening 236 is shaped such to direct flow passing therethrough in a second direction 246 which is parallel in course yet opposite to first direction 242. The first catheter includes a first lateral opening 234 located at first distal end region 222 proximally to first forward opening 232, and the second catheter includes a second lateral opening 238 located at second distal end region 226 proximally to second forward opening 228. First lateral opening 234 is shaped such to direct flow passing therethrough in a third direction 244 which has same direction about the median plane as first direction 242 yet is in opposite about the transverse plane. Likewise, second lateral opening 238 is shaped such to direct flow passing therethrough in a fourth direction 248 which has same direction about the median plane as second direction 246 yet is in opposite direction about the transverse plane.

Figure 3:
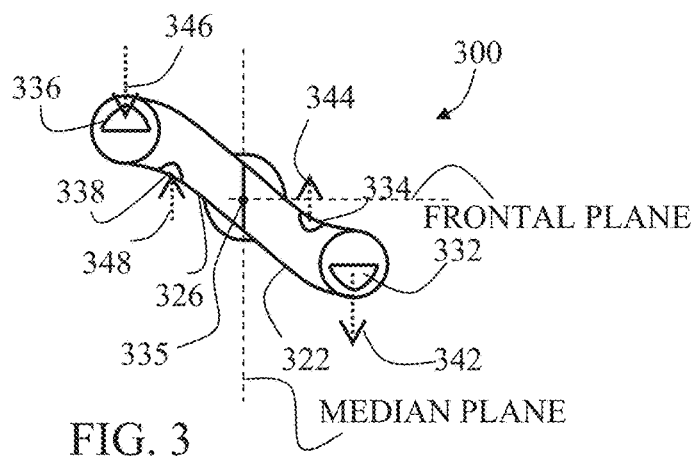
FIG. 3 schematically illustrates an exemplary dual-tip hemodialysis catheter assembly with diverging distal end regions, in accordance with embodiments of the present invention.

FIG. 3 schematically illustrates an exemplary dual-tip hemodialysis catheter assembly 300 with diverging distal end regions, in accordance with embodiments of the present invention. Catheter assembly 300 resembles catheter assembly 100 except that its end regions points to opposite directions with respect to a transverse plane in a Cartesian coordinate system and optionally twisted, at least in part, around a longitudinal axis 335. Catheter assembly 300 includes two partially merged catheters. The first catheter has a first distal end region 322 terminating in a first tip which includes a first forward opening 332 and the second catheter has a second distal end region 326 terminating in a second tip which includes a second forward opening 336. First distal end region 322 and second distal end region 326 extend substantially the same from the splitting line such that second tip 328 is in apposition to first tip 324, and are formed rotationally symmetric by overall size and shape and/or openings size, shape and/or distribution, one with the other, relatively to longitudinal axis 335. Optionally and additionally, first distal end region 322 and second distal end region 326 are distanced similarly about the transverse plane and/or optionally distanced similarly about the median plane.

Catheter assembly 300 includes distal openings for local blood dispersion and collection; all openings are shaped and distributed on distal end regions 322 and 326 while maintaining rotational symmetry around longitudinal axis 335. First forward opening 332 is shaped such to direct flow passing therethrough in a first direction 342 (shown in FIG. 3 as an outflow but can be reversed to inflow). As shown, first direction 342 is directed parallel to plane 330. Likewise, second forward opening 336 is shaped such to direct flow passing therethrough in a second direction 346 which is opposite to first direction 342. The first catheter includes a first lateral opening 334 located at first distal end region 322 proximally to first forward opening 332, and the second catheter includes a second lateral opening 338 located at second distal end region 326 proximally to second forward opening 328. First lateral opening 334 is shaped such to direct flow passing therethrough in a third direction 344 which is opposite to first direction 342. Likewise, second lateral opening 338 is shaped such to direct flow passing therethrough in a fourth direction 348 which is opposite to second direction 346.

Figure 4B:
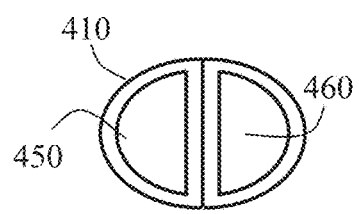
FIGS. 4A-4B schematically illustrate an exemplary dual-tip hemodialysis catheter deployed in a blood vessel, in accordance with embodiments of the present invention.
Figure 4A:
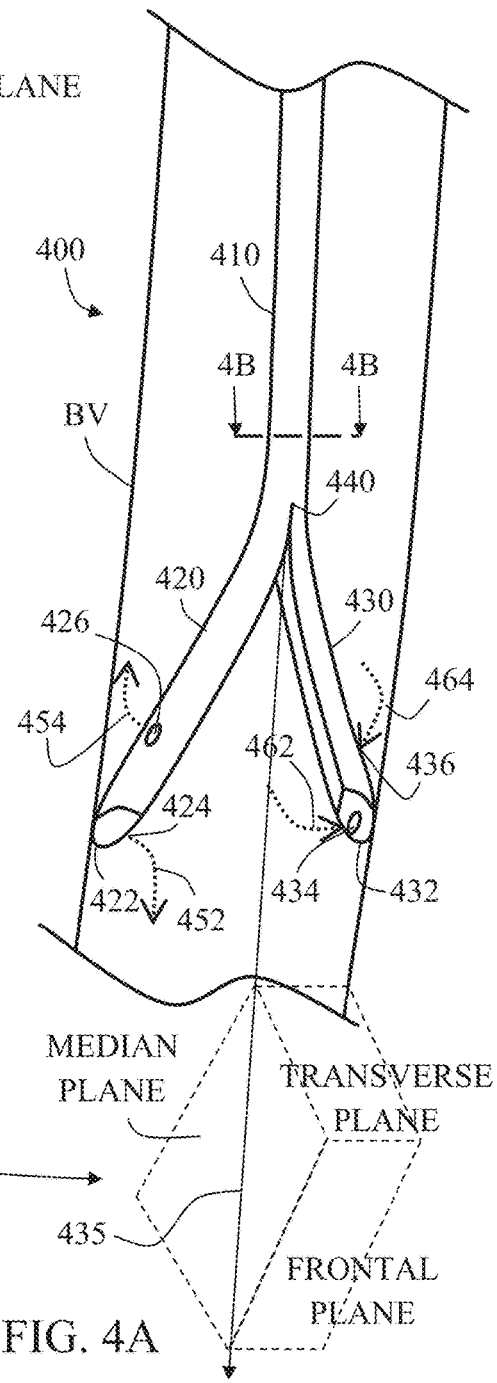

Reference is now made to FIGS. 4A-4B which schematically illustrate an exemplary dual-tip hemodialysis catheter 400 deployed in a blood vessel BV, in accordance with embodiments of the present invention. The blood vessel BV may be a large vein, optionally the superior vena cava or the right atrium. Catheter 400 includes an elongated body 410 which extends along a longitudinal axis 435 beginning with a unitary oval cross section and splitting at a junction 440 into a first distal end region 420 terminating in a first tip 422, and a second distal end region 430 terminating in a second tip 432. Elongated body 410 encloses a first lumen 450 extending between a first proximal port (not shown) and first tip 422, and a second lumen 460 extending between a second proximal port (not shown) and second tip 432. Lumens 450 and 460 are isolated one with the other such that fluids passing in one lumen will not communicate with the other lumen. Optionally, the lumens are formed similarly to a double-D formation in which a septum divides first lumen 450 and second lumen 460 along the elongated body length.

In some embodiments, catheter 400 is introduced into blood vessel BV covered with a sheath, optionally a peel-away sheath, which is then withdrawn fully or partially from catheter 400 and/or blood vessel BV, allowing first distal end region 420 and second distal end region 430 to separate one from each other and shift laterally with respect to longitudinal axis 435 up to a predetermined form. Preferably, first distal end region 420 and second distal end region 430 are formed in rotational symmetry one with the other relative to longitudinal axis 435. Optionally, first distal end region 420 and second distal end region 430 maintain at least some elastic properties and therefore tend to shift to their rotationally symmetric formation, at least when not stressed to a different formation.

Preferably, first distal end region 420 and the second end region 430 comprise a plurality of openings distributed and shaped in accordance with the rotational symmetry. The openings are opened to correlating lumen or lumens of the catheter and provide direct fluid communication between the lumen(s) and outside surroundings in blood vessel VB. Each of the first distal end region 420 and the second distal end region 430 comprising at least two openings shaped to direct flow passing therethrough in different directions.

First distal end region 420 comprising a first forward opening 424 located at first tip 422 and second distal end region 430 comprising a second forward opening 434 located at second tip 432. First forward opening 424 is shaped such to direct flow passing therethrough in a first course 452 having a first direction and second forward opening 434 is shaped such to direct flow passing therethrough in a second course 462 nonintersecting with the first course 452. First distal end region 420 also includes a first lateral opening 426 located proximally to first forward opening 424 and shaped such to direct flow passing therethrough in a third course 452 away from the first direction. Second distal end region 430 includes a second lateral opening 436 located proximally to second forward opening 434 and shaped such to direct flow passing therethrough in a fourth course 464, optionally in or towards the first direction, or optionally vertically to the first direction.

In some embodiments, catheter split is relative to a median plane in a Cartesian coordinate system, which is optionally parallel to longitudinal axis 435. In some embodiments, first course 452 and/or second course 462 and/or third course 454 and/or fourth course 464 has an orthogonal projection parallel to the median plane. Optionally, additionally or alternatively, first course 452 and/or second course 462 and/or third course 454 and/or fourth course 464 has an orthogonal projection parallel to a transverse plane orthogonal to the median plane in the Cartesian coordinate system. Optionally, alternatively or additionally, first course 452 and/or second course 462 and/or third course 454 and/or fourth course 464 has an orthogonal projection parallel to a frontal plane orthogonal to the median plane in the Cartesian coordinate system.

A known problem of catheter clotting in split-tip type catheters is at least partially caused by clot formation at the junction portion (i.e., splitting point/line/area) between the distal end regions. This point sees slow or low blood flow and thus, according to "Virchov's triad", is more likely to accommodate thrombosis formation. In some embodiments, dual tip dialysis catheters according to the present disclosures area are shaped such that, at a proper deployment in the body lumen, substantially no gap is formed in the junction portion. Optionally, dual-tip catheters according to the present disclosures are configured to undergo a scissor like movement from an aligned (closed) form to a deployed (opened) form. Optionally the catheter, or portion or member thereof, is elastic and becomes stressed when aligned and unstressed when deployed. Catheter aligning may be achieved in many fashions such as by using an external cover (e.g., a peel-away sheath) or an internal mandrel (e.g., guidewire or stylet), both preferably removable following catheter's deploying.

Figure 5:
FIG. 5 shows a commercially available hemodialysis split-tip catheter shortly following removal from a patient's body.

Reference is made to FIG. 5, which shows a commercially available hemodialysis split-tip catheter shortly following removal from a patient's body. The catheter in FIG. 5 is a double-D type split tip catheter that forms a dihedral angle or a "crack" between the inner planar walls of the two tips in the junction region, comprising an intersection line coinciding with the split line. In conventional catheters, the dihedral angle formed by the separating inner planar walls may be 10 to 30 degrees, and produces a crack in the junction region of the catheter. This crack is a region between the two facing surfaces of the catheter where they are separated by an amount sufficient to impede blood flowing past and over the surfaces, causing blood to pool in a no or low flow condition in the crack so as to produce a clotting risk. This clotting risk can be large when the distance between the two surfaces measured transverse to lumen extent (such distance 162 in FIG. 1A) over their facing portions is between 1 and 3 mm for a longitudinal extent of at least 3 mm. The inventor has devised a dual or split tip catheter that does not contain any such crack in its junction region. In one embodiment described further below, this is accomplished by reducing or eliminating the dihedral angle present in conventional split tip catheters. This crack-free catheter therefore poses less of a clotting risk than conventional catheter assemblies such as the one illustrated in FIG. 5.

Reference is made to FIGS. 6A-6C which schematically illustrate a catheter assembly 500, comprising a first catheter 510 and a second catheter 530 merged along a length 501. Length 501 comprises and/or follows a longitudinal axis 502. First catheter 510 includes a first proximal end region 512 comprising a first port 514, a first distal end region 516 terminating in a first tip 518, and a first wall 520 defining a first lumen 522 extending longitudinally therethrough between first port 514 and first tip 518. Second catheter 530 includes a second proximal end region 532 comprising a second port 534, a second distal end region 536 terminating in a second tip 538, and a second wall 540 defining a second lumen 542 extending longitudinally therethrough between second port 534 and second tip 538.

Catheter assembly 500 is configured to connect with a hemodialysis machine (connection can be facilitated via ports 514 and 524) such that one catheter can be set to deliver purified blood into the cardiovascular system and the other catheter can be set to draw blood therefrom, while occasionally the blood circulation may be reversed between these two catheters. In some embodiments, first lumen 522 and second lumen 542 are independent one to the other for facilitating simultaneous flow in opposite directions.

In some embodiments, first wall 520 and second wall 540 are longitudinally split from each other relative to a splitting plane 503 at a junction 504 positioned at or proximally to first distal end region 516 and second distal end region 536. Splitting plane 503 may be a median plane of the catheter assembly 500.

In some embodiments, first catheter 510 and/or the second catheter 530 comprises an elastic member or members 560 (or an elastic portion), about junction 504, having a non-stressed form at first distal end region 516 and second distal end region 536 being separated with each other along splitting plane 503 with no gap therebetween adjacent junction 504. By allowing splitting without a gap, the intention is that flow will not be stagnant at the junction and/or formation of thrombosis will be diminished or avoided.

In some embodiments, catheter assembly 500 includes removable aligning means, such as a removable cover 570 (e.g., a peel-away sheath) for aligning first distal end region 516 together with second distal end region 536 to longitudinal axis 502 (as shown in FIG. 6A). In some embodiments, upon removal of the aligning means, first distal end region 516 and second distal end region 536 voluntarily slide against each other, such as in a scissor-like movement, along splitting plane 503, optionally up to arriving at the non-stressed form of elastic member 560 (as shown in FIG. 6C).

Catheter assembly 500 may be of any form and shape of a split or dual tip catheter having symmetry or similarity in shape and/or size or not having symmetry or similarity in shape and/or size of its two distal end regions and/or openings distributed thereon. For demonstrative purposes the following description relates to two distal end portion having similarity and symmetry although it should be recognized that this is not a mandatory possibility as noted above. In some embodiments, second tip 538 and first tip 518 extend to substantially same length from junction 504. Optionally, second tip 538 is in apposition to first tip 518 when first distal end region 516 and second distal end region 536 are aligned. Optionally, second tip 538 is farthest to first tip 518 when elastic member 560 is unstressed.

In some embodiments, first distal end region 516 and second end region 536 are formed in rotational symmetry one with the other relative to longitudinal axis 502 and comprising a plurality of openings distributed and shaped in accordance with the rotational symmetry. In some embodiments, each of the first distal end region 516 and the second distal end region 536 comprises at least two openings shaped to direct flow passing therethrough in different directions. In some embodiments, first distal end region 516 comprises a first forward opening 524 located adjacent first tip 518 and second distal end region 536 comprises a second forward opening 544 located adjacent second tip 538. In some embodiments, first forward opening 524 is shaped such to direct flow passing therethrough in a first course 526 having a first direction. In some embodiments, second forward opening 544 is shaped such to direct flow passing therethrough in a second course 546. In some embodiments, forward openings 524 and 544 are designed such that second course 546 is nonintersecting with first course 524.

In some embodiments, first distal end region 516 comprises a first lateral opening 528 located proximally to first forward opening 524, and second distal end region 536 comprises a second lateral opening 548 located proximally to second forward opening 544. In some embodiments, first lateral opening 528 is shaped such to direct flow passing therethrough in a third course 529 directed away from the first direction (of first course 526). In some embodiments, second lateral opening 548 is shaped such to direct flow passing therethrough in a fourth course 549 directed in or towards the first direction (of first course 526). Optionally, additionally or alternatively, first lateral opening 528 is shaped such to direct flow passing therethrough vertically to the first direction of first course 526.

In some embodiments, first course 526 has an orthogonal projection parallel to splitting plane 503. Optionally, additionally or alternatively, first course 526 has an orthogonal projection parallel to a transverse plane—orthogonal to splitting plane 503 (being a median plane)—in same Cartesian coordinate system. Optionally, additionally or alternatively, first course 526 has an orthogonal projection parallel to a frontal plane—orthogonal to splitting plane 503 (being a median plane)—in same Cartesian coordinate system.

FIGS. 7A-7D schematically illustrate a hemodialysis catheter 600, comprising an elongated body 610 extendable along an assembly longitudinal axis 602, in accordance with embodiments of the present invention. In some embodiments, elongated body 610 splits longitudinally into a first distal end region 612, having a longitudinal axis 637 terminating in a first tip 614 and a second distal end region 616, having a longitudinal axis 639, terminating in a second tip 618, relative to a splitting plane 603, at a split 604. In some embodiments, elongated body 610 encloses a first lumen extending 620 between a first proximal port 622 and first tip 614, and a second lumen 624 extending between a second proximal port 626 and second tip 618.

A junction portion 656 is between a frontal plane 652 at split 604 and a frontal plane 654 distal to split 604. In this embodiment, the inner planar surfaces open and diverge in a scissors like manner that is generally parallel to the splitting plane (e.g. the median plane of FIG. 1). Therefore, in the junction region 628, the inner planar surfaces of the two lumens remain in contact even though the lumen walls are no longer extending parallel to one another. Different from some embodiments illustrated in FIGS. 1A-1C, FIGS. 7A-7D illustrate the catheter 600 that has a crack-free junction 628. For example, FIG. 1B illustrates the gap distance 162 as discussed above, but FIG. 7C illustrates the crack-free junction portion 656, which is approximately triangular when viewed from the side. The crack-free junction 656 may have a gap distance much less than the gap distance 162 (FIG. 1B) in its relaxed position. In conventional catheters, the gap distance 162 may be 1 to 3 mm at some distances between 5 mm and 20 mm from the split. In the catheter assembly of FIG. 7, this gap distance is less than 1 mm at all times in the junction region, and is advantageously less than 0.5 mm, or even more advantageously less than 0.1 mm, or even more advantageously the two planar inner lumen surface are in direct contact over all their facing surface in region 628.

It can also be seen in the end on view of FIG. 7C that the dihedral angle of conventional catheters is greatly reduced or eliminated. Preferably, the dihedral angle of the catheter of FIG. 7C is less than 10 degrees, more preferably less than 5 degrees, even more preferably less than 1 degree, and most preferably no dihedral angle is formed at all by the diverging planar inner lumen walls.

Catheter 600 is configured to connect with a hemodialysis machine (connection can be facilitated via ports 622 and 626) such that one catheter can be set to deliver purified blood into the cardiovascular system and the other catheter can be set to draw blood therefrom, while occasionally the blood circulation may be reversed between these two catheters. In some embodiments, first lumen 620 and second lumen 624 are independent one to the other for facilitating simultaneous flow in opposite directions. In some embodiments, a septum 632 divides first lumen 620 and second lumen 624 along a non-splitting length 634 of elongated body 610.

In some embodiments, elongated body 610 comprises the junction portion 628 (of elastic member, for example), about the split 604, having a non-stressed form at first distal end region 612 and second distal end region 614 when they are separated with each other along splitting plane 603, with no gap therebetween at the junction portion 656 (as shown in FIG. 7C). By allowing splitting without a gap, the intention is that flow will not be stagnant at the junction and/or formation of thrombosis will be diminished or avoided.

In some embodiments, hemodialysis catheter 600 comprises or may be provided with removable aligning means such as a removable cover 630 (e.g., an outer sheath such as a peel-away sheath), as shown in FIG. 7A, for aligning first distal end region 612 together with second distal end region 616 to the assembly longitudinal axis 602. In some embodiments, upon removal of the aligning means, first distal end region 612 and second distal end region 616 can voluntarily slide against each other, such as in a scissor-like movement, along splitting plane 603, optionally up to arriving at the unstressed form of the crack-free junction 628.

Catheter 600 may be of any form and shape of a split or dual tip catheter having symmetry or similarity in shape and/or size or not having symmetry or similarity in shape and/or size of its two distal end regions and/or openings distributed thereon. For demonstrative purposes the following description relates to two distal end portion having similarity and symmetry although it should be recognized that this is not a mandatory possibility as noted above. In some embodiments, second tip 618 and first tip 614 extend to substantially same length from the split 604. Optionally, second tip 618 is in apposition to first tip 614 when first distal end region 612 and second distal end region 616 are aligned. Optionally, second tip 618 is farthest to first tip 614 when elastic 628 is unstressed.

In some embodiments, first distal end region 612 and second distal end region 616 are formed in rotational symmetry one with the other relative to the assembly longitudinal axis 602 and comprising a plurality of openings distributed and shaped in accordance with the rotational symmetry. In some embodiments, each of the first distal end region 612 and the second distal end region 616 comprises at least two openings shaped to direct flow passing therethrough, in different directions. In some embodiments, first distal end region 612 comprises a first forward opening 636 located adjacent first tip 614 and second distal end region 616 comprises a second forward opening 638 located adjacent second tip 618. In some embodiments, first forward opening 636 is shaped such to direct flow passing therethrough in a first course 640 having a first direction. In some embodiments, second forward opening 638 is shaped such to direct flow passing therethrough in a second course 642 nonintersecting with first course 640.

In some embodiments, first distal end region 612 comprises a first lateral opening 644 located proximally to first forward opening 636, and second distal end region 616 comprises a second lateral opening 646 located proximally to second forward opening 638. In some embodiments, first lateral opening 644 is shaped such to direct flow passing therethrough in a third course 648, optionally directed away from the first direction. In some embodiments, second lateral opening 646 is shaped such to direct flow passing therethrough in a fourth course 650, optionally directed in or towards the first direction (of first course 640). In some embodiments, first lateral opening 644 is shaped such to direct flow passing therethrough vertically to the first direction (of first course 640). In some embodiments, first course 640 has an orthogonal projection parallel to splitting plane 603. Optionally, splitting plane 603 is a median plane of the hemodialysis catheter. In some embodiments, first course 640 has an orthogonal projection parallel to a transverse plane—orthogonal to splitting plane 603 (being a median plane)—in same Cartesian coordinate system. Optionally additionally or alternatively, first course 640 has an orthogonal projection parallel to a frontal plane—orthogonal to splitting plane 603 (being median plane)—in same Cartesian coordinate system.

Figure 8A:
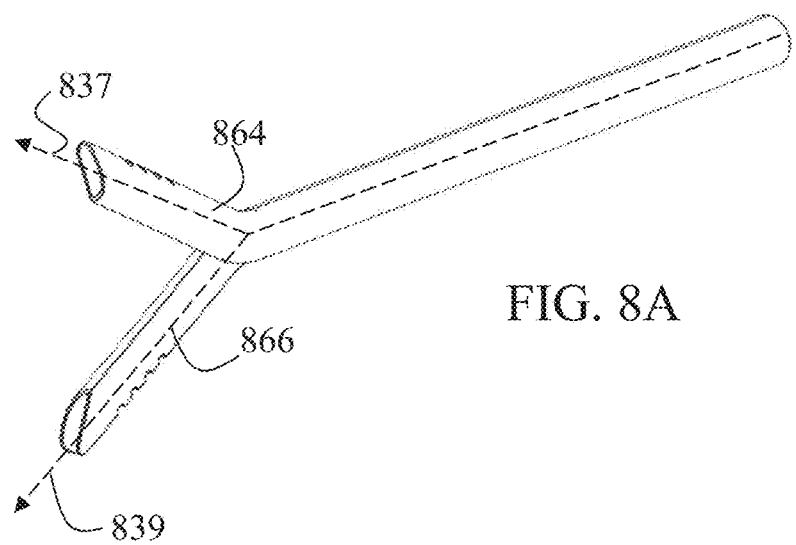
FIGS. 8A-8E are perspective views of a hemodialysis catheter in and out of a sheath according to some embodiments.
Figure 8B:
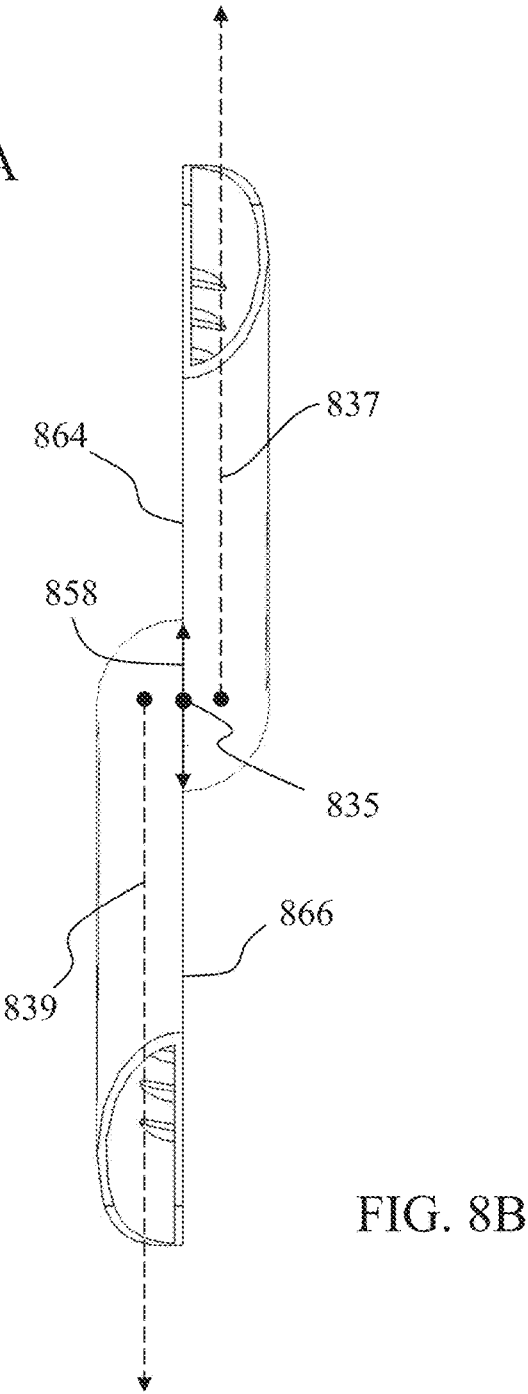

Reference is made to FIGS. 8A-8E, which illustrate perspective views of a hemodialysis catheter in and out of a sheath according to some embodiments. FIGS. 8A and 8B show a catheter assembly with a first lumen, having a longitudinal axis 837 and a first lumen wall 864, and a second lumen, having a longitudinal axis 839 and a second lumen wall 866. The illustrated embodiment has a crack-free junction 835 substantially similar to the crack-free junction 628 (FIG. 7C). The first and second lumen walls 864, 866 may be approximately on the same plane as the median plane 858, which is substantially similar to the splitting plane 603 (FIGS. 7A-7D) in its relaxed position, for example. Although the first and second longitudinal axes 837, 839 of the lumens diverge from the transverse plane (as defined above in FIGS. 1B and 1C), they may remain approximately the same distance from the median or splitting plane in the junction region as they diverge. In this embodiment, as contrasted with the configuration of FIG. 1, the lumens diverge mostly or wholly away from the transverse plane (as defined in FIGS. 1B and 1C) rather than mostly or wholly away from the median plane (as defined in FIGS. 1B and 1C). In some embodiments at least one lumen diverges from the transverse plane such that the tip is at least one centimeter from the transverse plane. In some embodiments, both lumens diverge from the median plane less than 5 mm farther from the median plane at their tips. It is to be noted that although the first and second lumen walls 864, 866 may be in contact and on the same median plan 858 at the junction portion 656 (FIG. 7C), the first and second lumen walls 864, 866 distally beyond the junction portion 656 (FIG. 7C) may be free to deviate from the median plane 858 or the splitting plane 603 (FIGS. 7A-7D).

Figure 8C:
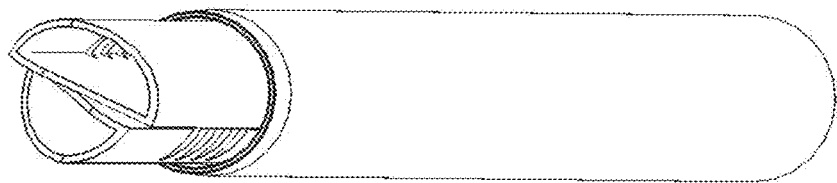
Figure 8D:
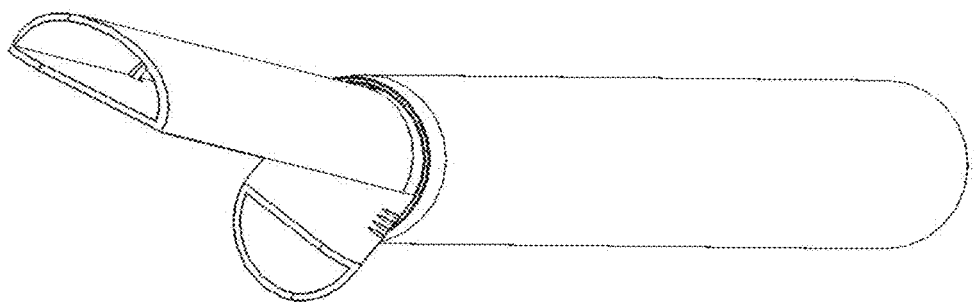
Figure 8E:
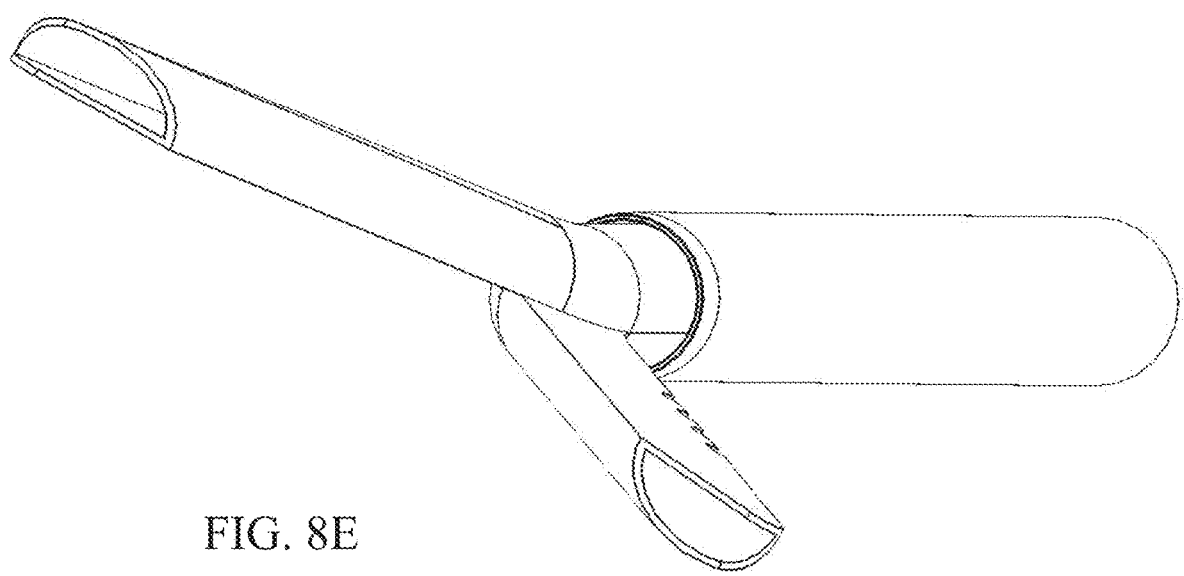

FIGS. 8C-8E show a catheter assembly with a removable cover (e.g., a peel-away sheath), substantially similar to the removable cover 630 (FIGS. 7A-7B). FIG. 8C illustrates the two distal portions of the catheter assembly substantially aligned with each other as the removable cover holds the two distal portions together. As the two distal portions slide out of the removable cover as illustrated in FIGS. 8D-8E, the two distal tips may move away from each other to their relaxed positions in a scissor-like movement.

Reference is made to FIGS. 9A-9B, which illustrate perspective views of another embodiment of a hemodialysis catheter according to some embodiments. FIG. 9A illustrates a catheter with a crack-free junction substantially similar to the ones illustrated in FIGS. 7A-8E. As discussed in connection with the lumen walls 864, 866 of FIGS. 8A-8B, the two distal portions beyond the junction portion 656 (FIG. 7C), may not have the same wall plane. Furthermore, as illustrated in FIG. 9B, the two distal portions beyond the junction portion 656 (FIG. 7C) may not have straight longitudinal axes (such as 837, 839) extending from those of the junction portion 652 (FIG. 7C). The two distal portions beyond the junction portion 656 (FIG. 7C) in FIG. 9B are curved in their relaxed positions so that the two distal portions are twistedly positioned while being longitudinally symmetric by its longitudinal assembly axis (similar to 602 (FIG. 7C)). In another embodiment, the two distal portions may move further away from the median plane providing the catheter assembly to be less twisted than as illustrated in FIG. 9B.

Reference is now made to FIGS. 10A-10G which schematically illustrate different scenarios representing possible exemplary steps in a method for forming a dual-tip catheter 1000, in accordance with embodiments of the present invention.

FIG. 10C shows a preformed part 1010 for forming catheter 1000. FIGS. 10A and 10B shows two possible scenarios in a method for forming preformed part 1010. As shown in FIG. 10A, a first preformed member 1001, a second preformed member 1002 and a third preformed member 1003 are collected. First preformed member 1001 encloses a plurality of lumens (in this example—lumens 1004 and 1005) extending therealong and opened at ends 1006 and 1007 thereof. Second preformed member 1002 encloses one lumen 1008 extending therealong and opened at ends 1009 and 1011 thereof. Third preformed member 1003 encloses one lumen 1012 extending therealong and opened at ends 1013 and 1014 thereof.

A shown in FIG. 10B, a first straight mandrel 1015 is inserted through lumen 1004 and lumen 1008, and a second straight mandrel 1016 is inserted through lumen 1005 and lumen 1012, and the three preformed members can be aligned and/or approximated over the first and second straight mandrels 1015 and 1016, as needed. Second preformed member 1002 and third preformed member 1003 are then welded to first preformed member 1001 to form preformed part 1010 in the shape of an elongated body. In some embodiments, lumen 1004 of first preformed member 1001 and lumen 1008 of second preformed member 1002 forms a first passage 1017. In some embodiments, lumen 1005 of first preformed member 1001 and lumen 1012 of third preformed member 1003 forms a second passage 1018.

FIG. 10C shows a finalized version of preformed part 1010 provided for forming catheter 1000. Preformed part 1010 comprises of an elongated body 1019, extendable along a longitudinal axis 1020, and is longitudinally split relative to a splitting plane 1021 at a junction 1022 into a first distal end region 1023 terminating in a first tip 1024 and a second distal end region 1025 terminating in a second tip 1026. Elongated body 1019 encloses first passage 1017 extending along longitudinal axis 1020 and opened at first tip 1024, and second passage 1018 extending along longitudinal axis 1020 and opened at second tip 1026. In some embodiments, elongated body 1019 comprises an elastic portion (or elastic member) across the junction, optionally elongated body 1019 is elastic along most or all its length, optionally radially elastic and/or optionally axially elastic.

In some embodiments, elongated body 1019 is formed of a fluid sealed material whereby first passage 1017 forms a first lumen and second passage 1018 forms a second lumen sealed to the first lumen. Optionally, a septum divides the first lumen and the second lumen along a non-splitting length of elongated body 1019. The fluid sealed material may include polymeric material such as silicone rubber or polyurethane, for example a polycarbonate-based thermoplastic polyurethanes (e.g., Carbothane™).

In some embodiments the preformed members are readily provided with lumens in a final cross section. In other embodiments, the lumens of the preformed members are shaped to a final cross section using the straight mandrels. In some such other embodiments, the first, second and/or third preformed members, 1001, 1002 and 1003, or the welded elongated body 1019, are heated such that first passage 1017 is shaped in accordance with outer boundaries of first straight mandrel 1015, and second passage 1018 is shaped in accordance with outer boundaries of second straight mandrel 1016.

Figure 10D:
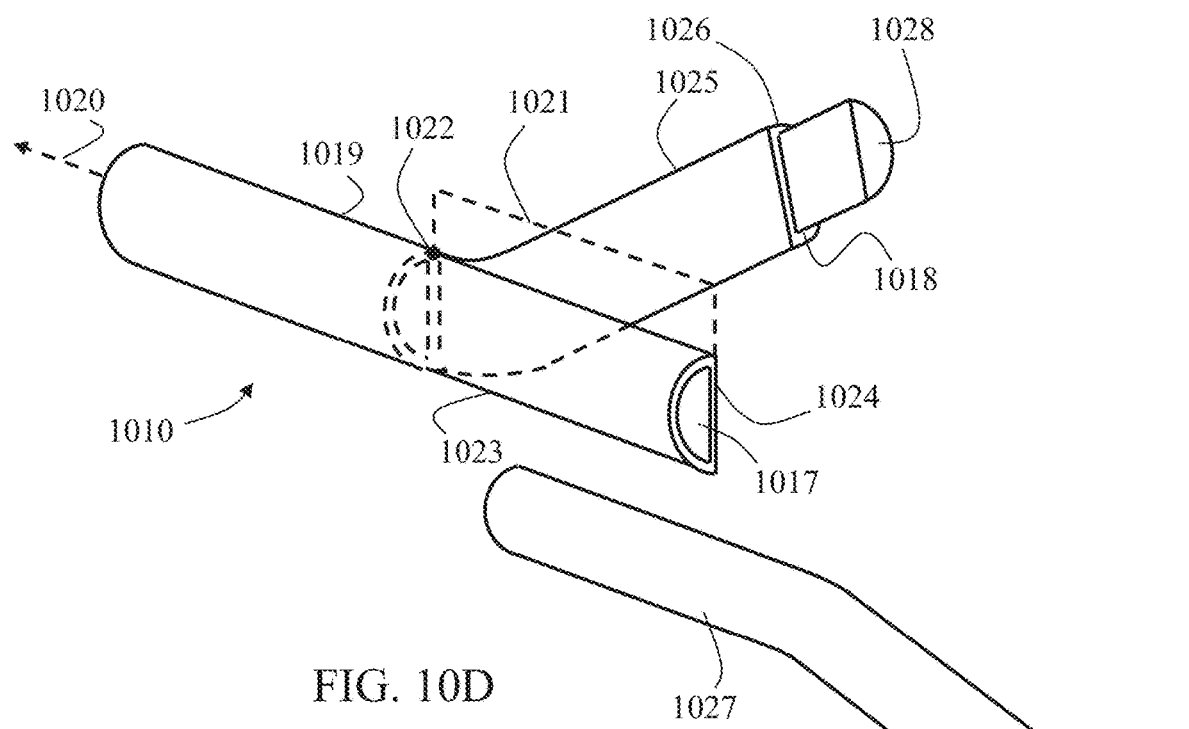
Figure 10E:
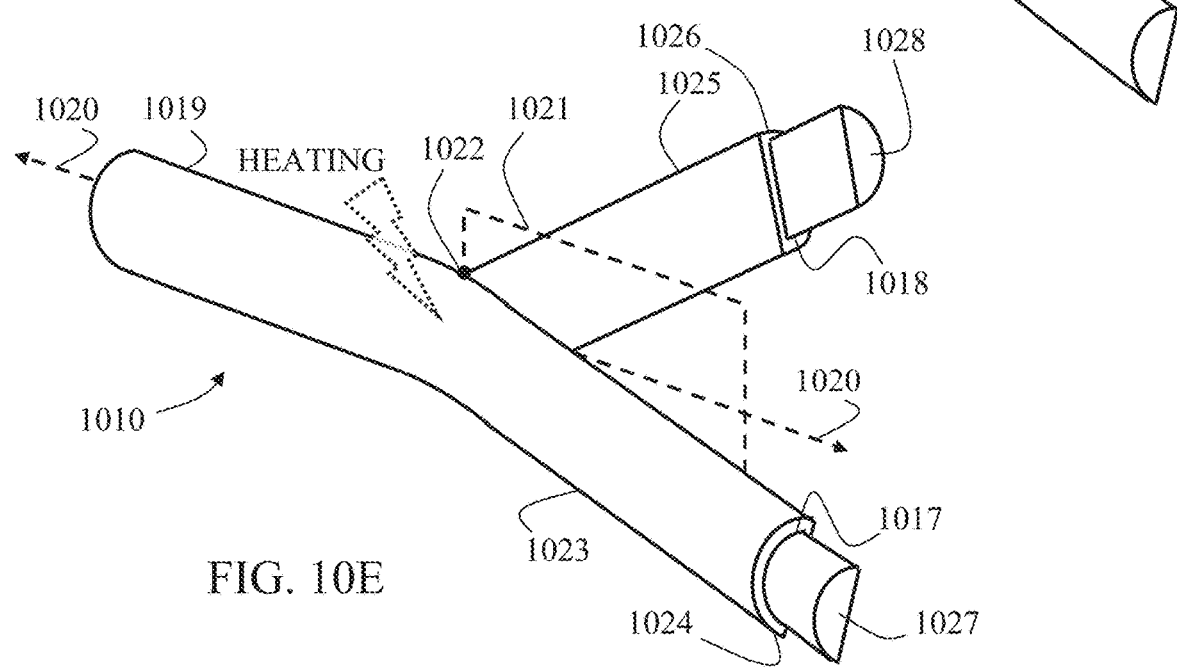

Contoured mandrels are then used in shaping catheter 1000 to its final form. Referring to FIG. 10D, a first contoured mandrel 1027 is inserted in first passage 1017 and a second contoured mandrel 1028 is inserted in second passage 1018, such that first end region 1023 is held in a first contour imposed by first contoured mandrel 1027 (as shown in FIG. 10D) and second end region 1025 is held in a second contour imposed by second contoured mandrel 1028 (shown in FIG. 10E). Elongated body 1019 is then treated for relieving internal stresses (illustrated in FIG. 10E). Optionally, said treating includes at least one of heat treatment, chemical treatment, hardening, and plastic deformation, optionally creating elastic resistivity to a deviation from the non-stressed form. In some embodiments, elongated body 1019 is heated such that first passage 1017 is shaped in accordance with outer boundaries of first contoured mandrel 1027 and second passage 1018 is shaped in accordance with outer boundaries of second contoured mandrel 1028.

Figure 11A:
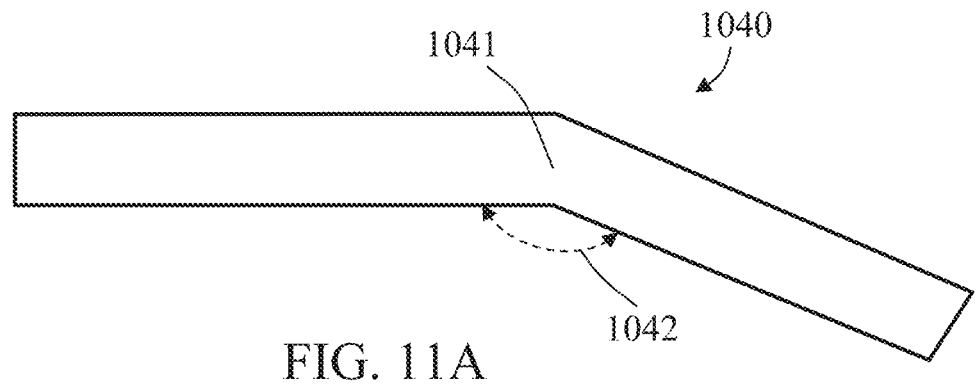
FIGS. 11A-11C schematically illustrate side views of exemplary contoured mandrels, in accordance with embodiments of the present invention.
Figure 11B:
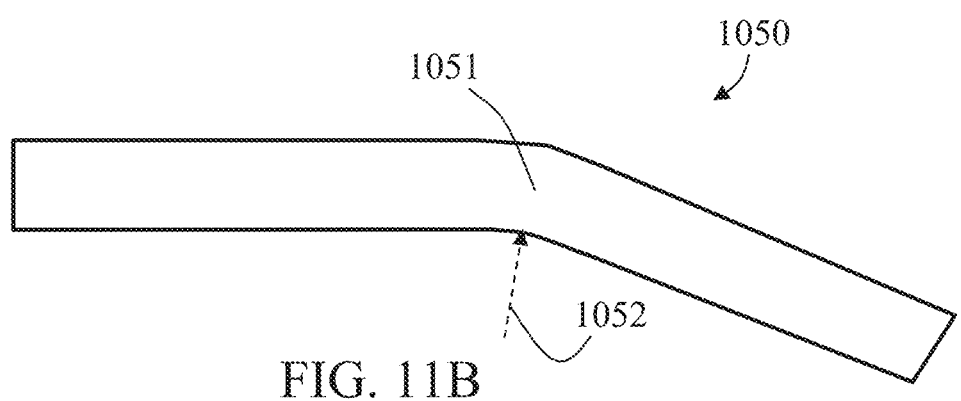
Figure 11C:
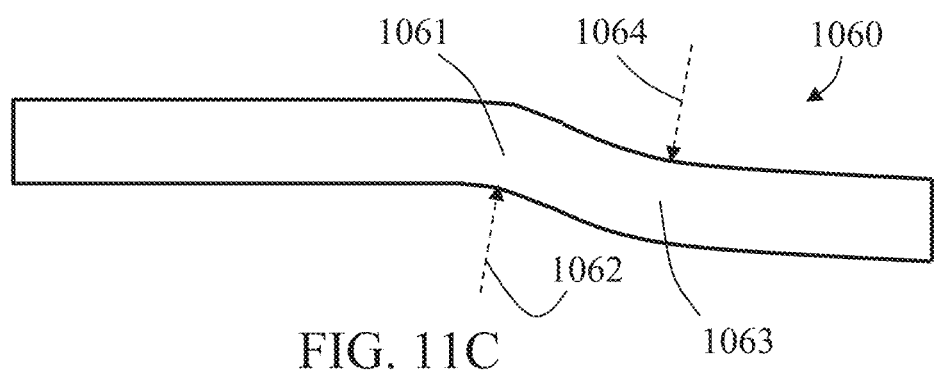

In some embodiments, each of first contoured mandrel 1027 and second contoured mandrel 1028 is fixedly angled or curved along length thereof. FIGS. 11A-11C schematically illustrate side views of exemplary contoured mandrels, in accordance with embodiments of the present invention. FIG. 11A shows an angled mandrel 1040 that is fixedly angled at portion 1041 along its length thereby forming angle 1042. FIG. 11B shows a curved mandrel 1050 being fixedly curved in a single portion 1051, along its length, having a radius of curvature 1052. FIG. 11C shows a second curved mandrel 1060 being fixedly curved in a first portion 1061, along its length, having a first radius of curvature 1062, and in a second portion 1063, distal to first portion 1061, having a second radius of curvature 1064. In some embodiments, first contoured mandrel 1027 is congruent or geometrically similar about corresponding angles or curvatures thereof, to second contoured mandrel 1028.

Figure 10F:
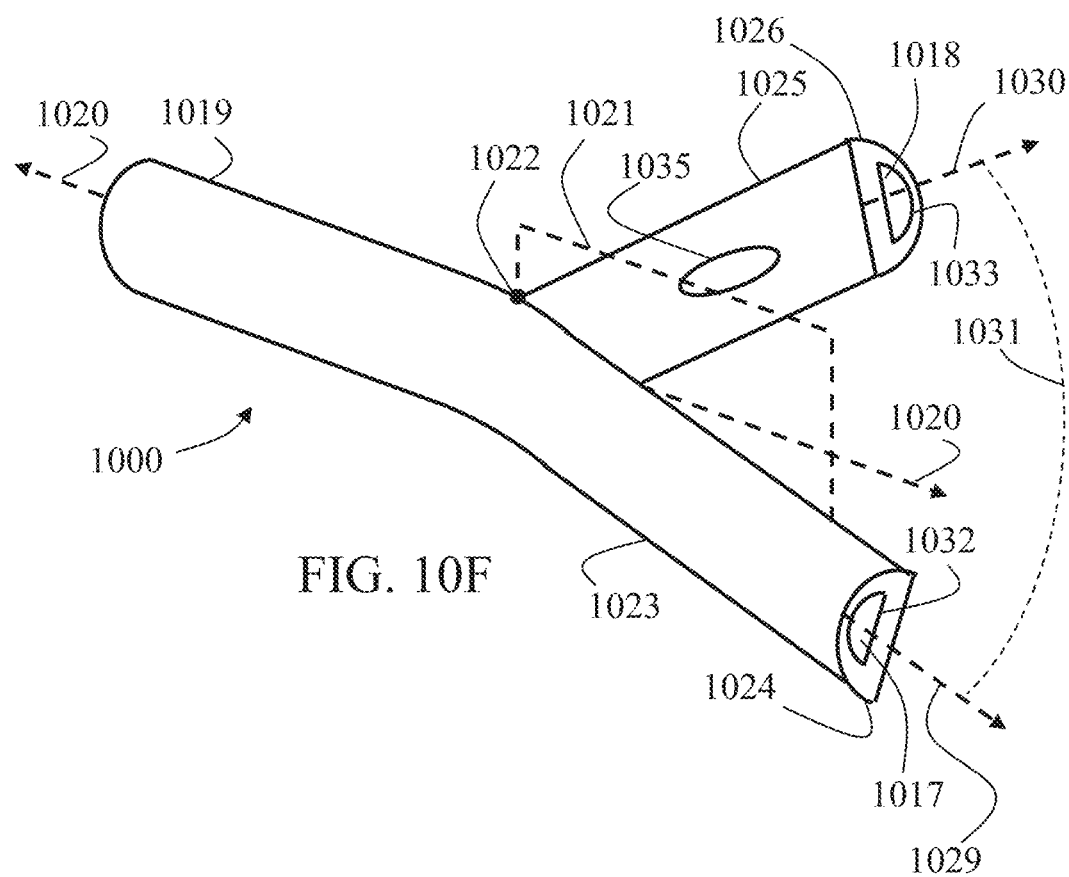

Referring back to FIGS. 10A-10G, first contoured mandrel 1027 is then removed from first passage 1017 and second contoured mandrel 1028 is removed from second passage 1018. As shown in FIG. 10F, following removal of the contoured mandrels, elongated body 1019 in its non-stressed form has first end region 1023 and second end region 1025 separated with each other along splitting plane 1021 with no gap therebetween adjacent junction 1022. Elongated body 1019 in its non-stressed form has first tip 1024 pointed towards a first direction 1029 and second tip 1026 pointed towards a second direction 1030 angled to first direction 1029, relative to splitting plane 1021, optionally forming an angle 1031 therebetween with junction 1022 in splitting plane 1021. Angle 1031 may be at least 15°, optionally at least 30°, optionally at least 45°, optionally 45° to 90°.

In some embodiments, first end region 1023 held in the first contour and second end region 1025 held in the second contour form rotational symmetry one with the other relative to longitudinal axis 1020. Also shown in FIG. 10F are openings formed and/or shaped in at least one of the end regions. Optionally, each of the first distal end region 1023 and the second distal end region 1025 comprises at least one opening distributed and shaped in accordance with the rotational symmetry, optionally at least two openings shaped to direct flow passing therethrough in different directions. As shown, first distal end region 1023 comprises a first forward opening 1032 located adjacent to first tip 1024 and a first lateral opening (not shown) located proximally to first forward opening 1032. Second distal end region 1025 comprises a second forward opening 1033 located adjacent to second tip 1026 and a second lateral opening 1035 located proximally to second forward opening 1033. Optionally, first forward opening 1032 is shaped such to direct flow passing therethrough in a first course nonintersecting with a flow in a second course directed by second forward opening 1033.

Figure 10G:
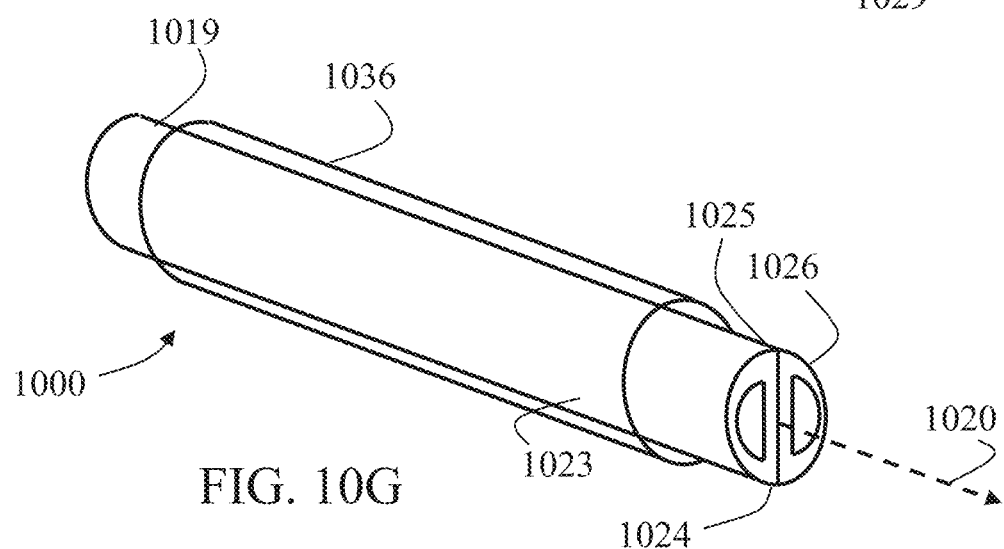

Catheter 1000 is optionally provided to the user with a removable cover, as shown in FIG. 10G. As shown, removable aligning means 1036 are coupled to catheter 1000 for aligning first distal end region 1023 together with second distal end region 1025 to longitudinal axis 1020. Optionally, second tip 1026 is in apposition to first tip 1024 when first distal end region 1023 and second distal end region 1025 are aligned. Upon removal of aligning means 1036, due to elastic characteristics of catheter 1000, first distal end region 1023 and second distal end region 1025 can voluntarily slide against each other, such as in a scissor-like movement, along splitting plane 1021, up to the non-stressed form (shown in FIG. 10F). Optionally, removable aligning means 1036 includes a removable cover such as a peel away sheath.

Reference is made to FIGS. 12A-12D which schematically illustrate different scenarios representing possible exemplary steps in another method for forming a dual-tip catheter 1100, in accordance with embodiments of the present invention. FIG. 12A shows a preformed part 1110 provided for forming catheter 1100. Preformed part 1110 is formed of a meshed structure, comprising at least one helically wound filament. The filament is optionally pliable and/or elastic and can be made from metal, polymer, carbon and/or glass, or other. Preformed part 1110 can be provided as a pre-preg (i.e. pre-impregnated) component having a polymeric matrix already present in a partially cured state with the meshed structure. Alternatively, preformed part 1110 may be provided bare and be impregnated and/or coated in a later stage.

Preformed part 1110 comprises of an elongated body 1119, extendable along a longitudinal axis 1120, and is longitudinally split relative to a splitting plane 1121 at a junction 1122 into a first distal end region 1123 terminating in a first tip 1124 and a second distal end region 1125 terminating in a second tip 1126. Elongated body 1119 encloses first passage 1117 extending along longitudinal axis 1120 and opened at first tip 1124, and second passage 1118 extending along longitudinal axis 1120 and opened at second tip 1126. In some embodiments, elongated body 1119 comprises an elastic portion across the junction, optionally elongated body 1119 is elastic along most or all its length, optionally radially elastic and/or optionally axially elastic. Optionally, elastic properties of the entire device are determined according to filaments elasticity and/or mesh design.

Optionally, contoured mandrels are used in shaping catheter 1100 to its final form (mandrels are not shown; final form is shown in FIG. 12B). A first contoured mandrel is inserted in first passage 1117 and a second contoured mandrel is inserted in second passage 1118, such that first end region 1123 is held in a first contour imposed by first contoured mandrel and second end region 1125 is held in a second contour imposed by second contoured mandrel.

Elongated body 1119 is then treated for relieving internal stresses. Optionally, said treating includes at least one of heat treatment, chemical treatment, hardening, and plastic deformation, optionally creating elastic resistivity to a deviation from the non-stressed form. In some embodiments, elongated body 1119 is heated such that first passage 1117 is shaped in accordance with outer boundaries of first contoured mandrel and second passage 1118 is shaped in accordance with outer boundaries of second contoured mandrel.

Preformed part 1110 may then be impregnated and/or coated with a polymeric solution, such that elongated body 1119 is formed of a fluid sealed material whereby first passage 1117 forms a first lumen and second passage 1118 forms a second lumen sealed to the first lumen. Optionally, a septum divides the first lumen and the second lumen along a non-splitting length of elongated body 1119. The fluid sealed material may include polymeric material such as silicone rubber or polyurethane, for example a polycarbonate-based thermoplastic polyurethanes (e.g., Carbothane™).

The contoured mandrels can then be removed from first passage 1117 and second passage 1118. As shown in FIG. 12C, following removal of the contoured mandrels, elongated body 1119 in its non-stressed form has first end region 1123 and second end region 1125 separated with each other along splitting plane 1121 with no gap therebetween adjacent junction 1122. Elongated body 1119 in its non-stressed form has first tip 1124 pointed towards a first direction 1129 and second tip 1126 pointed towards a second direction 1130 angled to first direction 1129, relative to splitting plane 1121, optionally forming an angle 1131 therebetween with junction 1122 in splitting plane 1121. Angle 1131 may be at least 15°, optionally at least 30°, optionally at least 45°, optionally 45° to 90°.

In some embodiments, first end region 1123 held in the first contour and second end region 1125 held in the second contour form rotational symmetry one with the other relative to longitudinal axis 1120. Also shown in FIG. 12C are openings formed and/or shaped in at least one of the end regions. Optionally, each of the first distal end region 1123 and the second distal end region 1125 comprises at least one opening distributed and shaped in accordance with the rotational symmetry, optionally at least two openings shaped to direct flow passing therethrough in different directions. As shown, first distal end region 1123 comprises a first forward opening 1132 located adjacent to first tip 1124 and a first lateral opening (not shown) located proximally to first forward opening 1132. Second distal end region 1125 comprises a second forward opening 1133 located adjacent to second tip 1126 and a second lateral opening 1135 located proximally to second forward opening 1133. Optionally, first forward opening 1132 is shaped such to direct flow passing therethrough in a first course nonintersecting with a flow in a second course directed by second forward opening 1133.

Catheter 1100 is optionally provided to the user with a removable cover (e.g., a peel-away sheath), as shown in FIG. 12D. As shown, removable aligning means 1136 are coupled to catheter 1100 for aligning first distal end region 1123 together with second distal end region 1125 to longitudinal axis 1120. Optionally, second tip 1126 is in apposition to first tip 1124 when first distal end region 1123 and second distal end region 1125 are aligned. Upon removal of aligning means 1136, due to elastic characteristics of catheter 1100, first distal end region 1123 and second distal end region 1125 can voluntarily slide against each other, such as in a scissor-like movement, along splitting plane 1121, up to the non-stressed form (shown in FIG. 12C). Optionally, removable aligning means 1136 includes a removable cover such as a peel away sheath.

Referring back to embodiments of exemplary split-tip hemodialysis catheter 600, shown in FIGS. 7A-7D, and a variation thereof shown in FIGS. 13A-13C, a distal portion 660 of elongated body 610 thereof includes first distal end region 612, terminating in first tip 614 having a first forward opening 636, and second distal end region 616, terminating in second tip 618 having a second forward opening 638. In some embodiments, the variation of catheter 600 shown in FIGS. 13A-13C has no side openings along each of distal end regions 612 and 616 thereof. Optionally and additionally, this variation has only first and second forward openings 636 and 638 as the only openings within the distal portion 660 of the catheter, which can be utilized for withdrawing blood from, or delivering purified blood to, the target site (e.g., right atrium of a subject's heart).

Elongated body 610 encloses first lumen 620 which extends from first proximal port 622 to first forward opening 636, and second lumen 624 which extends from second proximal port 626 to second forward opening 638. First lumen 620 and second lumen 624 split from a shared boundary 661 along a non-splitting length 634 of elongated body 610, at a distal junction 628, into first distal end region 612 with the first tip 614 and second distal end region 616 with the second tip 618. Furthermore, first lumen 620 and second lumen 624 split from the shared boundary 661, at a proximal junction 662, into a proximal portion 668 of elongated body 610 which is separated into a first proximal end region 663, terminating in the first proximal port 622, and a second proximal end region 664, terminating in the second proximal port 626.

catheter 600 is configured to have first and second distal end regions 612 and 616 elastically diverge from alignment along a splitting plane SP to regain a relaxed configuration of catheter 600, of elongated body 610 or distal portion thereof. First and second distal end regions 612 and 616 can be delivered through blood vasculature (e.g., including the superior vena cava) to the right atrium of a subject when confined to alignment with each other, then be released to diverge according to the splitting plane in the right atrium.

Catheter 600 is configured for connecting with a hemodialysis machine 666 (shown, for example, in FIG. 14D) via proximal ports 622 and 626, such that one lumen can be set to deliver purified blood into the cardiovascular system and the other lumen can be set to draw blood therefrom. In some embodiments, catheter 600 is configured, labeled or/and applicable, for allocating one of the lumens particularly for withdrawing blood and for allocating the other lumen particularly to deliver purified blood.

In a relaxed and straighten form of elongated body 610, when it is not subject to stresses forcing it into elastic deformations, distal end regions 612 and 616 diverge one relative to the other, and relative to rest of elongated body 610 (along its non-split length portion 634). FIG. 7C shows junction region 628, originating at split 604, in which proximal-most portions of distal end regions 612 and 616 (e.g., the inner planar surfaces of the two lumens therein) are in contact, when in full divergence (e.g., when the lumen walls do not extend parallel to one another), in a fully relaxed form of elongated body 610. In some embodiments, these proximal-most portions of distal end regions 612 and 616 can move (e.g., slide) relative to each other as other portions of distal end regions 612 and 616. In some other embodiments, these proximal-most portions of distal end regions 612 and 616 are fixated (e.g., glued, soldered, casted or extruded together) one to the other around/about junction region 628, so that each of distal end regions 612 and 616 can move independently from the other only distally to junction region 628. In both scenarios, distal end regions 612 and 616 can be elastically deformed into alignment, relative to each other or/and relative to rest of elongated body 610, and spring back into a less constrained/a more relaxed form (and up to a fully relaxed form, as previously described) when aligning means are removed therefrom, for example.

When shifting distal portion of catheter 600 from an aligned (more stressed) form to a deployed (less stressed) form, inner planar surfaces 665 of first lumen 620 and second lumen 624 open and diverge voluntarily (due to elastic properties of the catheter), optionally in a scissors like manner that is generally parallel to the splitting plane (such as the median plane shown in FIG. 1, for example). In the relaxed form, the inner planar surfaces of the two lumens remain in contact adjacent to distal junction (split) 604 even though the lumen walls are no longer extending parallel to one another relative to planes other than the splitting plane.

Figure 16:
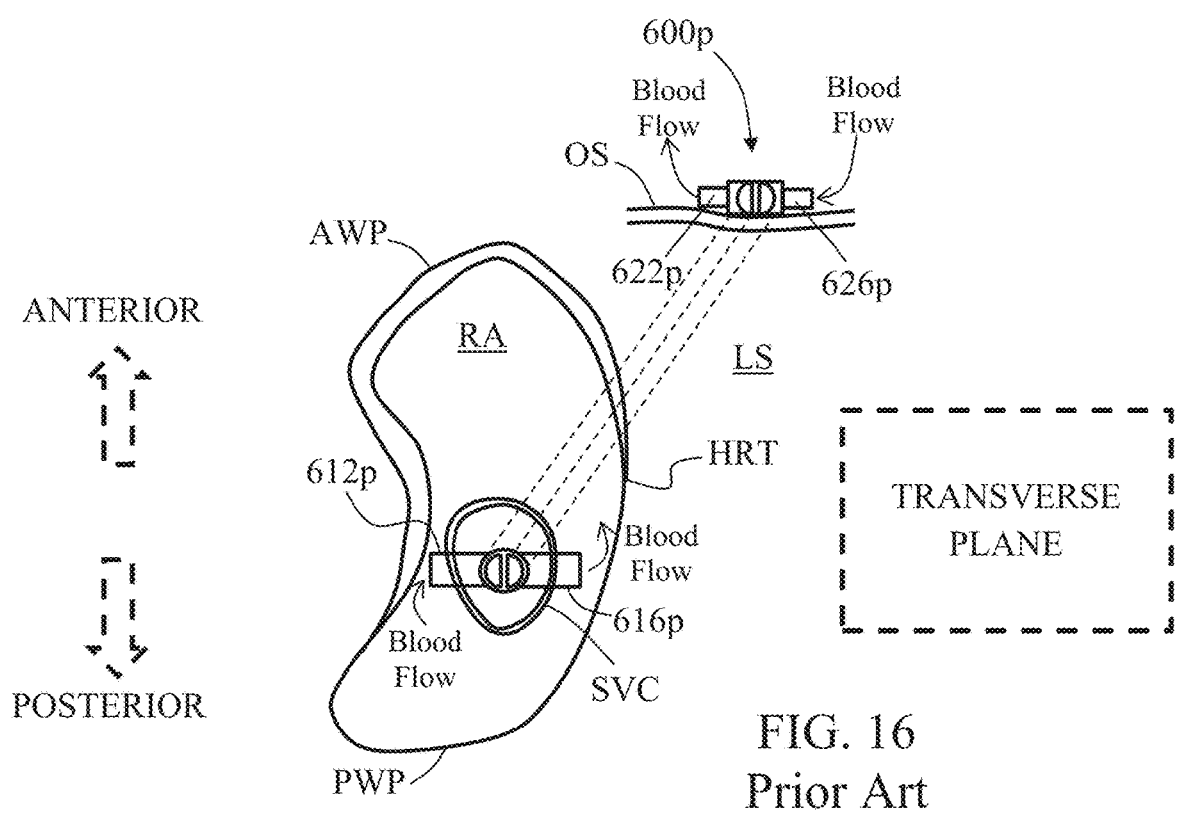
FIG. 16 schematically illustrates a prior art split-tip catheter deployed in a right atrium in same transverse section superior view shown in FIG. 15C, in accordance with embodiments of the present invention.

A reason to have a split-tip catheter with a 'gapless split' (i.e., minimal to no gap is formed adjacent junction, contrary to prior art split-tip catheters, such as prior art split-tip catheter 600p illustrated in FIG. 16, for example), can be to diminish or prevent stagnant blood flow at the junction and/or that formation of thrombosis will be diminished or avoided. Catheter 600 is therefore configured to possess a crack-free (i.e., gapless) distal junction 604 when in the deployed (non-aligned) form, with a minimal to no gap within the boundaries of junction region 628, or within a distance of at least 5 mm, optionally about 20 mm, from distal junction (split) 604. Optionally, in case there is a slight gap or crack along 20 mm distance from distal junction 604, the gap distance is less than 0.5 mm, or less than 0.1 mm. Optionally, the two planar inner lumen surfaces 665 are in direct contact over all their facing surfaces from adjacent to distal junction 604 to 10 mm, 15 mm, or 20 mm, or more, distally therefrom, or even up to adjacency to first tip 614 and second tip 618. As such, the dihedral angle of catheter 600 at its deployed, or even fully relaxed, form, is less than 10 degrees, optionally less than 5 degrees, optionally less than 1 degree, either within junction region 628 or/and between junction region 628 and tips 614 and 618. In some embodiments, no dihedral angle is formed at all by the diverging planar inner lumen walls.

Figure 14A:
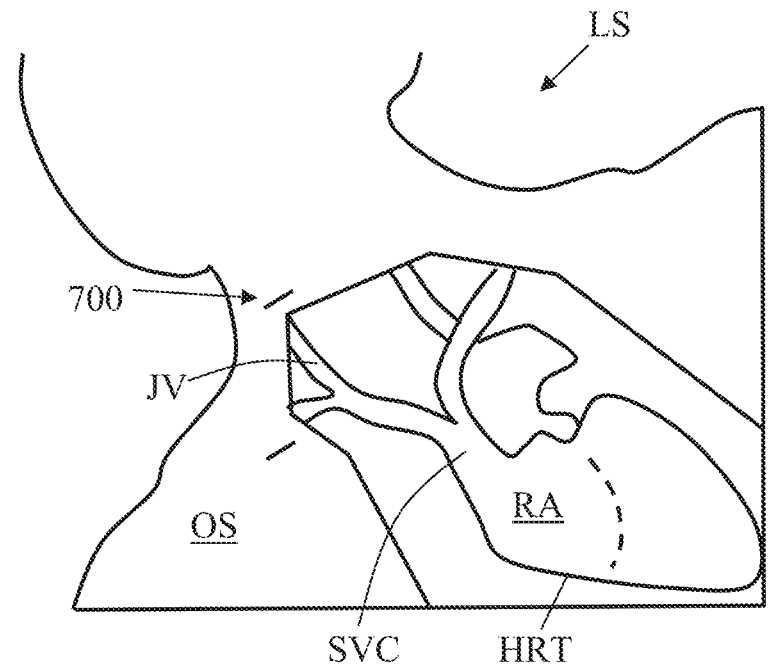
FIGS. 14A-14D schematically illustrate different scenarios representing possible exemplary steps in a method for deploying the exemplary split-tip catheter of FIGS. 13A-C in a right atrium in a heart of a live subject, in accordance with embodiments of the present invention.
Figure 14B:
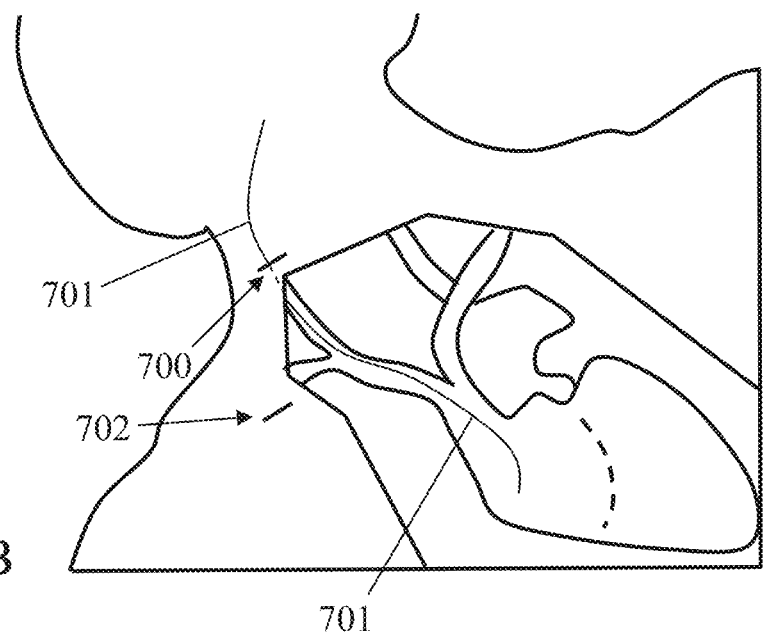
Figure 14C:
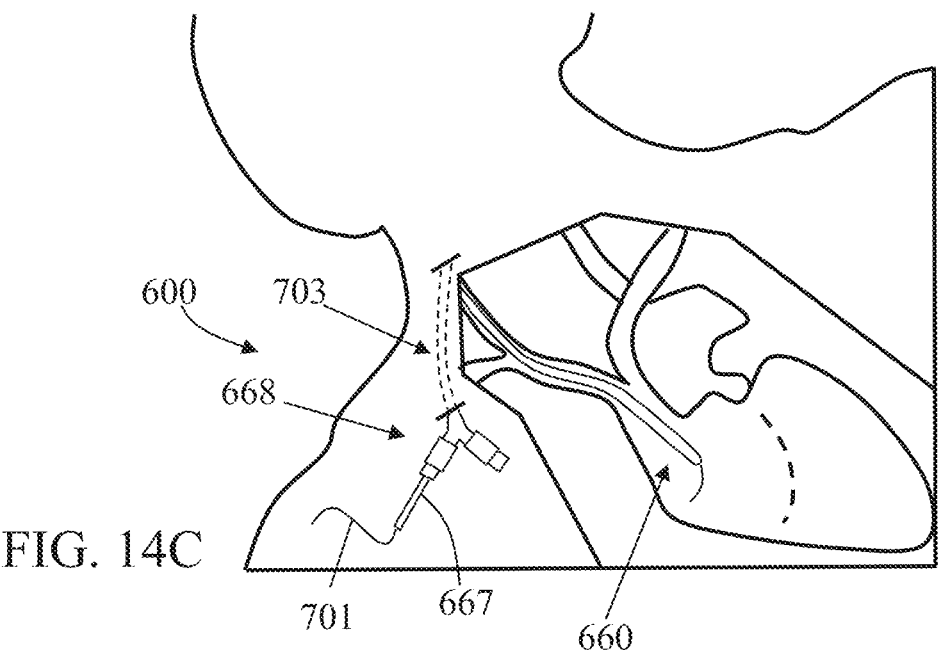
Figure 14D:
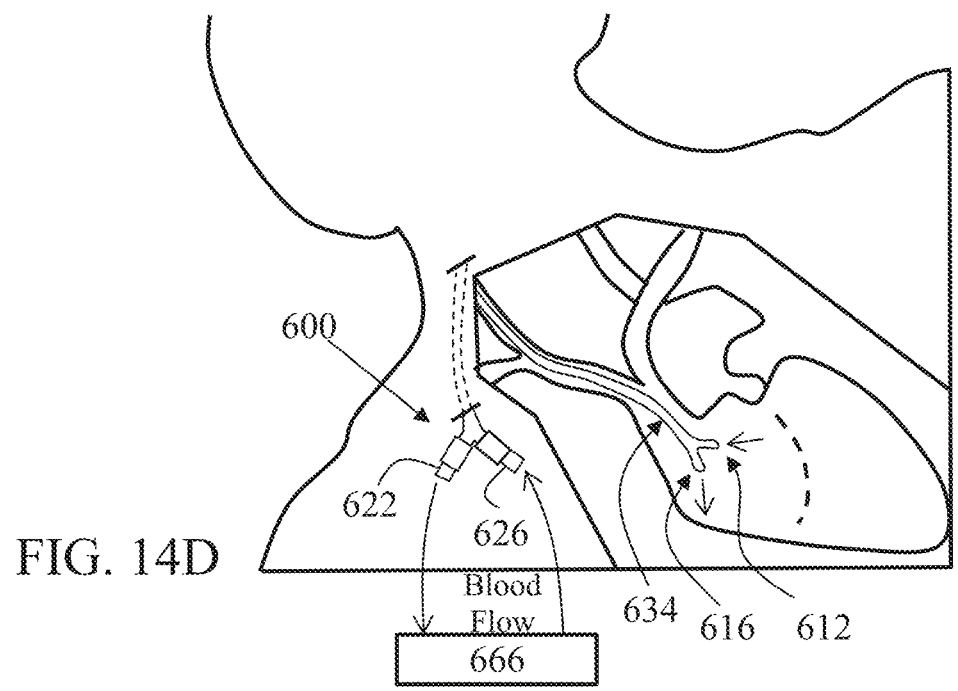

In some embodiments, catheter 600 is provided with removable aligning means for bringing into approximation or/and aligning first lumen 620 and first tip 614 with second lumen 624 and second tip 618, such as by using a removable cover 630 (for example an outer sheath or a peel-away sheath), as shown for example in FIG. 7A, or by an internal aligning or/and stiffening element 667 when extending in at least one of the lumens, as shown for example in FIG. 14C, or by using a removable or/and dismantlable cap for holding the tips together.

Upon removal of the aligning means, first distal end region 612 and second distal end region 616 can diverge elastically, optionally by voluntarily sliding against each other such as in a scissor-like movement, along the splitting plane SP, optionally up to arriving at the deployed (less stressed or completely unstressed) form of the crack-free distal junction 604. In some embodiments, second tip 618 and first tip 614 extend to substantially same length from the distal junction 604. Optionally, second tip 618 is in apposition to first tip 614 when first distal end region 612 and second distal end region 616 are aligned. Optionally, second tip 618 is farthest to first tip 614 when distal portion of the elongated body 610 is in a deployed (e.g., unstressed) form.

In some embodiments, a first variation of catheter 600 has distal portion thereof incorporating forward openings with no side openings. In some other embodiments, other variations of catheter 600 have a distal portion which includes side openings. In some embodiments, the first catheter variation may be more advantageous for use in long-term or chronic implantations, while the second variation may be used in same or in other scenarios. Side openings are present in most dialysis catheters with the aim to overcome potential failures in the process of removing blood from right atrium due to obstruction of the forward opening (e.g., positional occlusion).

Nevertheless, chronic hemodialysis catheters with side openings may be more prone to long-term complications such as clotting, poor function and infections, so they are associated with higher infection rates and lower probability of catheter survival. Implementation of side openings may be subject to one or more of the following limitations: (1) catheter locking solution may not reach the distal portion of the catheter, as it will be spilled out through the side opening(s), thus contributing to clot formation at the tip; (2) the side openings have rough edges therefore providing anchoring sites for clots formation; (3) clots which have been created at the catheter tip between dialysis sessions cannot be aspirated, as the aspiration is performed through the side hole, leaving the clot at the tip intact; and (4) intimal damage to the adjacent vessel or heart lining, possibly due to the aspiration and direction of flow through the side openings, may contribute to vascular damage that might cause clot formation and vascular stenosis.

In some embodiments, catheter 600 is configured without side openings at distal portion thereof, and is configured to facilitate long-term blood removal from the body in the dialysis process, by establishing selective orientation of the forward openings having anatomical advantages, to thereby diminish or fully prevent occlusion of one or both forward openings. Reference is now made to FIGS. 14A-14D, which schematically illustrate different scenarios representing possible exemplary steps in a method, for deploying exemplary split-tip hemodialysis catheter 600 in a right atrium RA, in a heart HRT of a live subject LS. Insertion of catheter 600 is optionally part of a placement protocol of a chronic catheter or central line. Local anesthesia is first applied to a first, surgically made, entry site 700, afterwards a guidewire 701 (e.g., a 0.038" 'J' or 'Straight' stainless steel guidewire) is provided via first entry site 700, into and through a vein JV (which may be any of internal jugular vein, external jugular vein, subclavian vein or femoral vein, for example) or/and the superior vena cava SVC, and into the right atrium RA.

Guidewire 701 may be introduced using an introducer needle, then the introducer needle can be removed from first entry site 700 after verifying a chosen guidewire placement. A second entry site 702 may be formed if a subcutaneous path (tunnel) 703 is preferred for holding portion of catheter 600 therein. Second entry site 702 is optionally formed below first entry site 700 (in a direction generally away from patient's head). For forming subcutaneous path 703, the skin area between first and second entry sites 700 and 702 is locally anesthetized and tunneled using a surgical tunneler. For placing catheter 600 through percutaneous pass 703, the catheter and the tunneler are passed across subcutaneous path 703 between second entry site 702 and first entry site 700. Afterwards, the tunneler is separated from catheter 600 and removed.

In order to deliver distal portion 660 of catheter 600 into right atrium RA, for example, it is first confined with aligning means, as suggested above, bringing the distal end regions and tips into alignment with non-split length portion 634 of elongated body 610. FIG. 14 demonstrate one possibility for delivering and deploying catheter 600, out of several other options, in which an internal stiffener 667 is used during delivery and until deployment of distal portion 660 in right atrium RA. Another possible delivery technique includes use of an outer sheath or cannula, as previously described, which is used for aligning distal ends regions of catheter 600 until they are brought into protrusion distally thereto. When an outer sheath or cannula are applied, guidewire 701 may be removed after the outer sheath or cannula are positioned, and catheter 600 can then be pushed through the outer sheath or cannula. When an internal stiffener or a cap is applied instead of outer sheath or cannula, guidewire 701 may be used for guiding catheter 600 with the internal stiffener or cap, and only then be removed, as schematically illustrated in FIG. 14.

In case a dilator is readily provided on guidewire 701 the dilator is first removed and then catheter 600 can be passed over guidewire 701 (or via an outer sheath or cannula) through first entry site 700 into the vasculature system and advanced until distal portion 660 thereof is inserted via superior vena cava SVC into the right atrium RA. Upon confirmed positioning, the aligning means and other possible delivery accessories can be removed leaving only catheter 600 in place, also allowing distal end regions 612 and 616 to shift into deployed form (e.g., by shifting voluntarily or/and elastically) in which they are diverged in different direction and become, each, non-aligned with non-split length portion 634 of elongated body 610. In case there are no deformation imposing external stresses (e.g., by space-confining surrounding anatomy), and if the distal end regions or/and distal portion 660 were elastically aligned with the removable aligning means, the deployed form of catheter 600 will be substantially or even fully unstressed (i.e., in a relaxed form). Following deployment, first lumen 620 and second lumen 624 can be properly conditioned, such as by aspirating blood, flushing saline, or/and introducing anticoagulant agent (e.g., Heparin) therethrough.

As may be demonstrated during deployment of catheter 600, or/and after it is fully deployed and fixated to the subject, the unique conceptual design of split-tip catheter 600 allows certain positioning and orientation of distal portion 660 (including the distal end regions and tips) within the right atrium, which the inventors found advantageous to currently known positioning outcomes resulting from designs of split-tip catheters known in the art. For example, the tip or/and forward opening of catheter 600, allocated for withdrawing blood, can be oriented and directed towards a relatively open space in the right atrium RA rather than towards a close wall portion which may be sucked into the forward opening, as the resulted orientation showed in FIG. 15B with respect to an exemplary prior art split-tip catheter.

Such orientation may be effected according to user selection, possibly under real time visualization of distal portion 660 in right atrium RA, or it may be predetermined according to catheter design and as a direct result of proximal end regions 663 and 664 orientation relative to outer surface OS (e.g., skin surface) of subject LS. In the latter case, based on exemplary catheter designs or/and methods of deployment thereof presented therein, by setting the splitting plane in a particular angular orientation to the separation plane of proximal end regions 663 and 664 (if the catheter is fully straighten and relaxed, for example), such features can determine or at least substantially contribute to at least one of: final spatial orientation of distal end regions 612 and 616, proximity of tips 614 and 618 to wall portions in the right atrium, and direction of blood flow from/to forward openings 636 and 638.

In the exemplary embodiment presented in the figures, the chosen splitting plane SP of the distal end regions 612 and 616 coincides with the median plane of catheter elongated body 610, while the separation of proximal end regions 663 and 664 is configured to follow along a transverse plane of catheter elongated body 610, and in opposite directions relative to the median plane of elongated body 610. Therefore, according to this example, by substantially paralleling the transverse plane of elongated body 610 with outer surface OS of the subject LS, upon deployment and fixation of catheter 600 to the subject body, the user (medical practitioner) determines the spatial arrangement of catheter distal portion 660 elements and their orientation in right atrium RA, which is derived partially or completely from angular orientation between (distal) splitting plane SP (e.g., catheter median plane) and (proximal) separation plane (e.g., catheter transverse plane).

In some embodiments, catheter 600 is delivered and deployed by orienting splitting plane SP to parallel or to form an acute angle with a sagittal plane crossing right atrium RA. A method for deploying catheter 600 also includes attaching a proximal portion of catheter 600 to outer surface of the subject with said first and second proximal end regions 663 and 664 appositionally arranged on subject's outer surface OS. In some such embodiments, orienting splitting plane SP includes directing catheter 600 such that splitting plane SP is perpendicular or oblique to subject outer surface OS.

In some embodiments, releasing first distal end region 612 from alignment with second distal end region 616 in right atrium RA is accomplished by allowing first end region 612 to diverge along splitting plane SP with first tip 614 shifting towards an anterior wall portion of right atrium RA. Attaching to the outer surface OS may involve configuring first proximal port 622 into pointing from proximal junction 662 towards a first direction. Releasing first distal end region 612 from alignment may involve configuring first tip 614 into pointing from distal junction 604 towards a second direction, different from the first direction in a tridimensional aspect. Optionally, the second direction is perpendicular to said first direction relative to a transverse plane crossing right atrium RA.

Figure 15A:
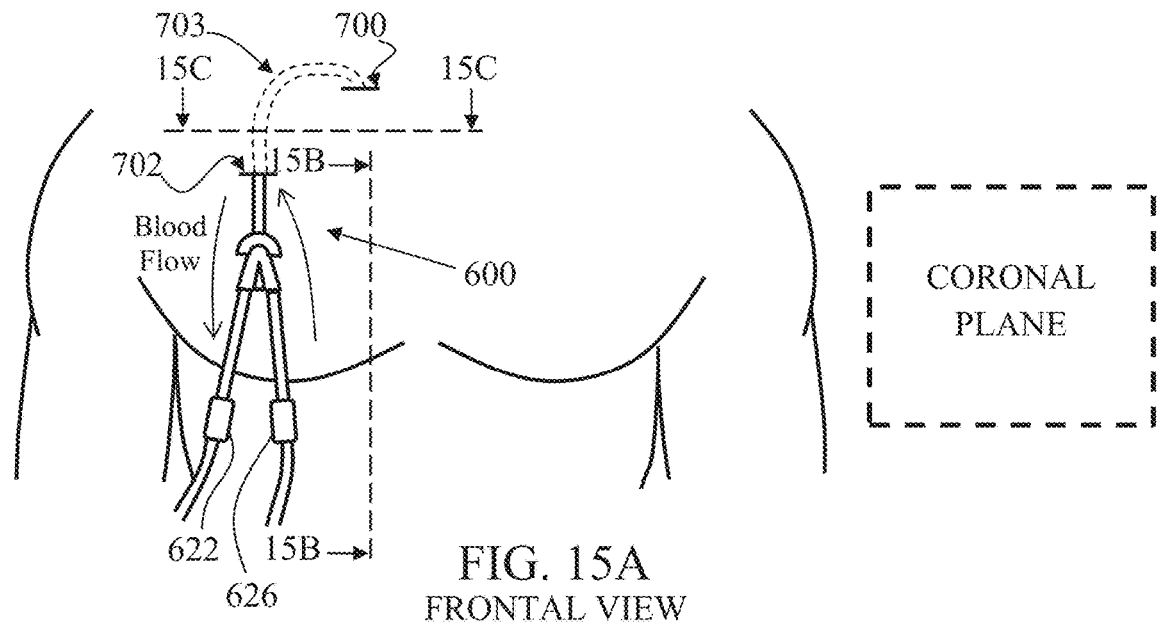
FIG. 15A schematically illustrates a frontal view relative to a coronal plane of a subject with the exemplary split tip catheter variation shown in FIGS. 13A-13C deployed in the right atrium, in accordance with embodiments of the present invention.
Figure 15B:
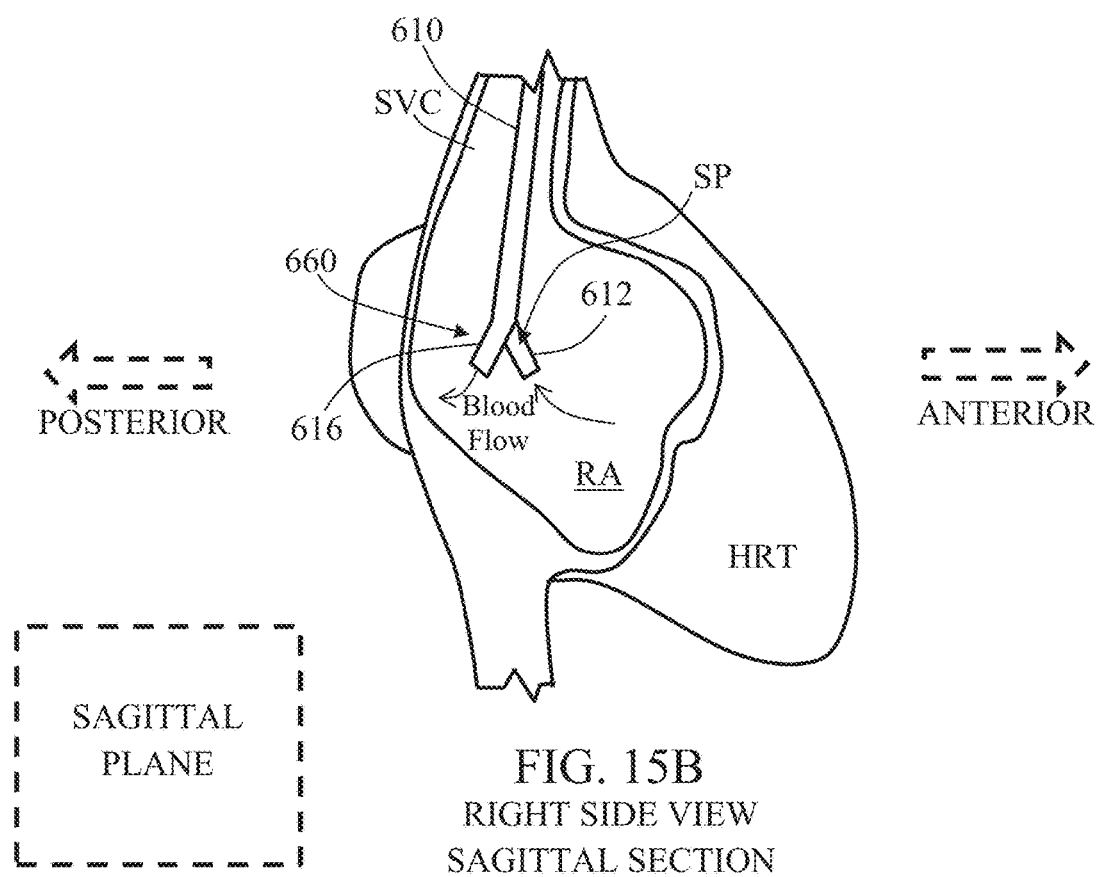
FIGS. 15B-15C schematically illustrate a sagittal section right side view (FIG. 15B) and a transverse section superior view (FIG. 15C) of the subject with the deployed split-tip catheter shown in FIG. 15A, in accordance with embodiments of the present invention.
Figure 15C:
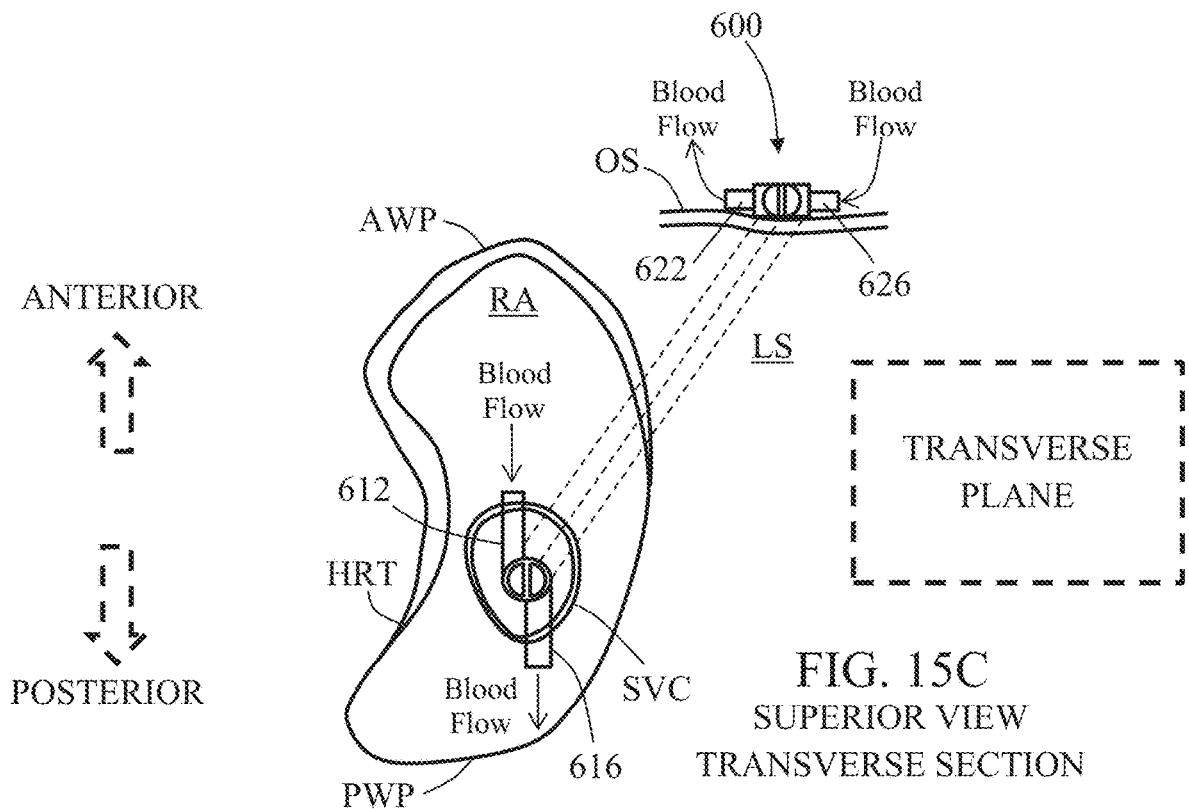

FIG. 15A schematically illustrate a frontal view of a fully implanted and tunneled catheter 600 in a live subject LS. FIG. 15B is a sagittal section right side view of catheter 600 in the position shown in FIG. 15A. FIG. 15C is a transverse sectional superior view of catheter 600 in the position shown in FIG. 15A. FIG. 16 illustrates an exemplary 'prior art' split-tip catheter 600*p* similarly deployed. As shown, there is an anatomical advantage in withdrawing blood from anterior region of the right atrium due to the relatively large space in front of the catheter distal end, while there is sufficient room left to deliver purified blood into the posterior region of the right atrium.

In some embodiments, catheter 600 is set such that blood is withdrawn from the right atrium RA through first forward opening 636, and purified blood is delivered via second forward opening 638. Catheter fixation to body includes attaching the proximal portion 668 of catheter 600 (which includes proximal junction 662 and proximal end regions 663 and 664) to outer surface OS of the live subject LS, by which first and second proximal ports 622 and 626 are laid in approximation (e.g., lay side-by-side) on outer skin surface of the live subject. Optionally, and as shown in FIG. 14 for example, fixating the catheter also includes laying a mid-portion 669 of the split-tip catheter 600 along subcutaneous path 703, the mid-portion 669 extends between proximal portion 668 and distal portion 660. Optionally, during or/and following catheter fixating, first and second lumens 620 and 624 remain straight, untwisted or/and unturned with each other, throughout, and relative to, shared boundary 661.

As shown in FIGS. 15A-15C and 16, while both pairs of proximal end regions, 622 and 626 of catheter 600 and 622p and 626p of prior-art catheter 600p, diverge along a coronal plane being substantially parallel to outer body surface OS, if under same delivery and deployment characteristics of the catheters in heart HRT, the distal end regions 612 and 616 are oriented in directions having anatomical advantage, rather than distal end regions 612p and 616p of prior-art catheter 600p, which are more prone to obstruction and failure.

Upon fixating the split-tip catheter 600 to the subject LS, first forward opening 636 is directed generally towards an anterior right atrium wall portion AWP, and second forward opening 638 is directed generally away from the anterior right atrium wall portion AWP. Particularly, following catheter fixating, second forward opening 638 is optionally directed generally towards a posterior right atrium wall portion PWP. Optionally, first distal end region 612 is directed from superior vena cava SVC generally towards anterior right atrium wall portion AWP, and second distal end region 616 is directed from superior vena cava SVC generally towards posterior right atrium wall portion PWP.

Optionally, and as shown particularly in FIG. 15B, first forward opening 636 is directed anteriorly along a sagittal plane of the subject's body, and second forward opening 638 is directed posteriorly along the sagittal plane of the subject's body. In contrast, FIG. 16 shows a common deployment of exemplary prior art split-tip catheter 600p in which both distal end regions 612p and 616p, carrying forward openings, are oriented sideways rather than in a posterior/anterior general direction, which makes this deployment more prone to dialysis failure due to suction of the right atrium or venous wall, positional occlusion, and/or malfunction, for example.

In some embodiments, exemplary split-tip catheters of the present invention and methods of deployment thereof can be applied to exchange (replace) a previously deployed hemodialysis catheter. A common phenomenon causing failures in function of long-term dialysis catheters is fibrin sheath formation, by covering and obstructing the openings of hemodialysis catheters. In prolonged implantation periods a naturally occurring fibrin sheath is gradually built around the catheter which is composed of thrombus, endothelial cells and collagen, with gradually changing in composition and mechanical properties depending on the duration of the catheter placement. Common treatment options include pharmacological and/or mechanical methods, the latter including catheter exchange, fibrin sheath disruption using guide wire and angioplasty balloon, and fibrin sheath stripping using snares.

FIGS. 17A-17F schematically illustrate different scenarios representing possible exemplary steps in a method for deploying split-tip catheter 600 in a structure FBS formed by naturally occurring fibrin sheath. Catheter 600 is optionally configured to have first and second distal end regions 612 and 616 elastically divergent from alignment by applying a maximal lateral force sufficient to cut through or pull apart a naturally occurring fibrin sheath, such as fibrin sheath structure FBS.

Figure 17A:
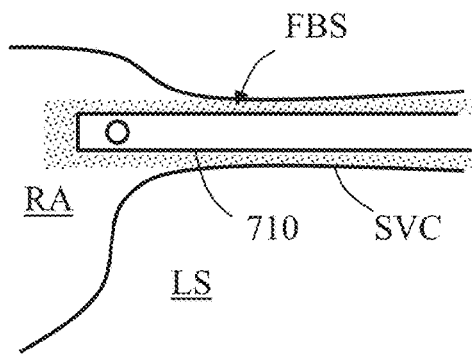
FIGS. 17A-17F schematically illustrate different scenarios representing possible exemplary steps in a method for deploying an exemplary split-tip catheter in a structure formed by naturally occurring fibrin sheath, in accordance with embodiments of the present invention.

FIG. 17A shows a hemodialysis catheter 710 after prolonged implantation in a superior vena cava and right atrium RA of a live subject LS, and is covered with fibrin sheath structure FBS which partially or fully obstructs its openings stationed in right atrium RA. This causes failure in hemodialysis treatments so hemodialysis catheter 710 is exchanged with split-tip catheter 600.

Figure 17B:
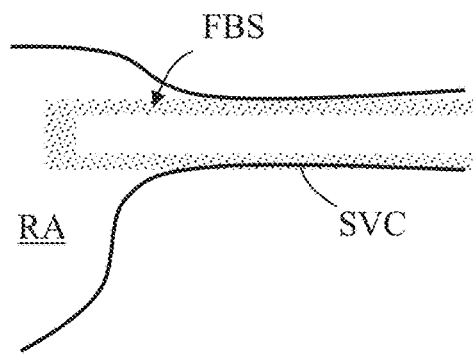
Figure 17C:
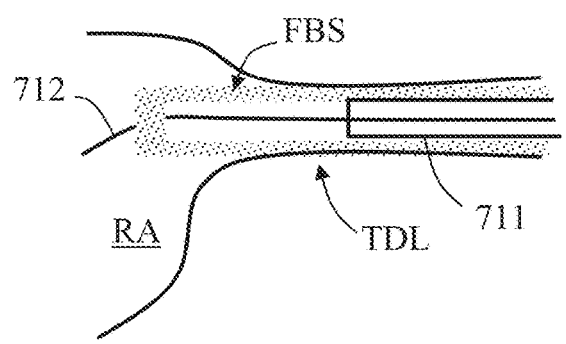

A generally tubular fibrin sheath structure FBS may remain at least partly intact after removing hemodialysis catheter 710, as illustrated in FIG. 17B, into which an outer sheath 711 is introduced over a guidewire 712 (FIG. 17C). Optionally, inner dimensions of fibrin sheath structure FSB and outer dimensions of outer sheath 711 cause tubular fibrin sheath structure to tightly fit over outer sheath 711. While first end region 612 is confined to alignment with second distal end region 616, said split-tip catheter 600 is passed in superior vena cava SVC via outer sheath 711.

Optionally and alternatively, no outer sheath is placed within fibrin sheath structure 710 as part of the delivery process, and another type of alignment means may be applied instead to align distal end regions of catheter 600 during its delivery. For example, guide wire 712 is first introduced through across hemodialysis catheter 700, then hemodialysis catheter 700 is removed over guidewire 712 while leaving guidewire in-place, and afterwards split-tip catheter 600 can be delivered and deployed by passing it over same guidewire 712. In this case, aligning means in a form of inner rod(s) or stylet(s) can be stationed within the catheter lumens being stiff enough to align the distal end regions of the catheter 600.

In some embodiments, catheter 600 is applicable for disrupting fibrin sheath structure FBS by selectively releasing distal end regions thereof to extend laterally and engage inner boundaries of the fibrin sheath structure by forces sufficient to break or cut through the fibrin sheath, for example. In some embodiments, maximal lateral force applicable by diverging of distal end regions 612 and 616 from alignment to each other is at least 50 gr, optionally at least 100 gr, optionally at least 500 gr, optionally at least 1 kg. Releasing of first and second end regions may include pushing the first and second distal end regions 612 and 616 to protrude out of outer sheath 711 while allowing first and second tips 614 and 618 to extend laterally from centerline of said outer sheath, to an extent sufficient to break portion of the fibrin sheath structure FBS.

Figure 17D:
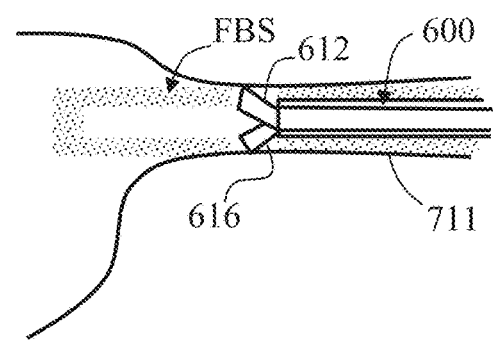
Figure 17E:
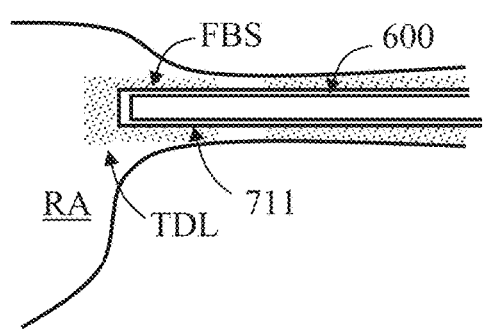
Figure 17F:
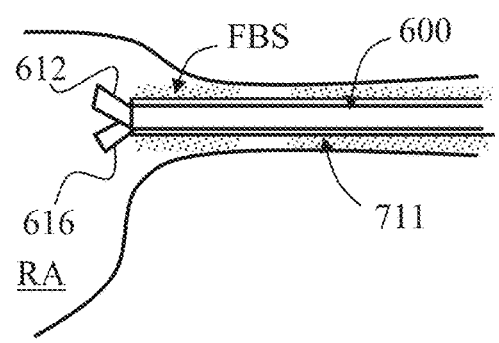

In order to disrupt fibrin sheath structure FBS in portions along blood vessels such as superior vena cava SVC, the outer sheath (or other aligning means) can be positioned adjacent to a target disruption location TDL of the fibrin sheath structure, and then releasing first end region 612 from alignment with second end region 616 to diverging along splitting plane SP, to thereby forcefully extend in lateral opposing directions (FIG. 17D). These steps of advancing outer sheath 711 to a target disruption location TDL and then advancing catheter 600 to protrude and locally disrupt (break) the fibrin sheath structure can be repeated along its length until reaching into the right atrium RA, so that outer sheath 711 is positioned in proximity to junction of superior vena cava SVC and right atrium RA, for example (FIG. 17E), and the catheter 600 is pushed to protrude therefrom allowing distal end regions to diverge and disrupt fibrin sheath structure with distal tips thereof (FIG. 17F).

In some embodiments, catheter 600 is utilized for disrupting a local fibrin sheath structure only in or adjacent to the right atrium for allowing proper usage thereof without obstructing its openings with the fibrin sheath. In some embodiments, similar process can be implemented for maintaining openings of catheter 600 patent or/and for clearing obstructing fibrin sheath by repeatedly aligning and releasing distal end regions 612 and 616, with optionally rotating the splitting plane to affect different peripheral portions of the tubular fibrin sheath structure.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method comprising:
   providing a split-tip catheter comprising a first lumen and a second lumen having a shared boundary from a proximal junction to a distal junction, the first lumen and the second lumen split at the distal junction into a first distal end region terminating in a first tip and a second distal end region terminating in a second tip, wherein the split-tip catheter is configured to have the first distal end region and the second distal end region elastically diverge from alignment along a splitting plane to regain a relaxed configuration;
   delivering the first distal end region confined to alignment with the second distal end region in a superior vena cava opened to a right atrium of a subject; and
   releasing the first distal end region from alignment with the second distal end region, in the right atrium, by allowing the first distal end region to diverge along the splitting plane with the first tip shifting toward an anterior wall portion of the right atrium.

2. The method according to claim 1, further comprising withdrawing blood from the right atrium through a first forward opening provided at the first tip.

3. The method according to claim 2, wherein the first distal end region is configured for withdrawing blood only from the first forward opening.

4. The method according to claim 1, further comprising:
   orienting the splitting plane to parallel or to form an acute angle with a sagittal plane crossing the right atrium.

5. The method according to claim 4, wherein the first lumen and the second lumen split at the proximal junction into a first proximal end region terminating in a first proximal port and a second proximal end region terminating in a second proximal port, the method further comprising:
   attaching a proximal portion of the split-tip catheter to an outer surface of the subject with the first proximal end region and the second proximal end region appositionally arranged on the outer surface of the subject.

6. The method according to claim 5, wherein the orienting step includes directing the split-tip catheter such that the splitting plane is perpendicular or oblique to the outer surface of the subject.

7. The method according to claim 5, wherein, following the attaching step, the first proximal port points from the proximal junction towards a first direction, and, following the releasing step, the first tip points from the distal junction towards a second direction, wherein the second direction is perpendicular to the first direction relative to a transverse plane crossing the right atrium.

8. The method according to claim 1, wherein the split-tip catheter is configured to have the first distal end region and the second distal end region elastically diverge from alignment by applying a maximal lateral force sufficient to cut through or pull apart a naturally occurring fibrin sheath,
   wherein the delivering step includes passing the split-tip catheter with the first distal end region and the second distal end region confined to alignment using removable aligning means through a tubular fibrin sheath structure;
   wherein the releasing step includes removing the removable aligning means from the first distal end region and the second distal end region for allowing the first tip and the second tip to extend laterally.

9. The method according to claim 8, wherein the delivering step includes positioning an outer sheath in the tubular fibrin sheath structure and passing the split-tip catheter in the outer sheath whereby inner boundaries of the outer sheath impose the alignment of the first distal end region with the second distal end region;
   wherein the releasing step includes pushing the first distal end region and the second distal end region to protrude out of the outer sheath to an extent sufficient to break a portion of the tubular fibrin sheath structure.

10. The method according to claim 8, wherein the maximal lateral force is at least 50 gr.

11. A split-tip catheter for hemodialysis comprising:
    a first lumen and a second lumen having a shared boundary from a proximal junction to a distal junction, the first lumen and the second lumen split at the distal junction into a first distal end region terminating in a first tip and a second distal end region terminating in a second tip:
    wherein the split-tip catheter is configured to have the first distal end region and the second distal end region elastically diverge from alignment along a splitting plane to regain a relaxed configuration.

12. The split-tip catheter according to claim 11, wherein the first distal end region is deliverable to a right atrium of a subject confined to alignment with the second distal end region using removable aligning means, and is configured for releasing from the removable aligning means in the right atrium, thereby diverging along the splitting plane with the first tip shifting towards an anterior wall portion of the right atrium.

13. The split-tip catheter according to claim 12, further comprising a first proximal port connectable to hemodialysis machine and having fluid communication with a first forward opening in the first tip,
    the split-tip catheter configured such that, after deployment thereof into extending through a subcutaneous path and a superior vena cava, with the first distal end region and the second distal end region provided in the right atrium, the first proximal port points from the proximal junction towards a first direction, and the first tip points from the distal junction towards a second direction, wherein the second direction is perpendicular to the first direction relative to a transverse plane crossing the right atrium.

\* \* \* \* \*